(12) United States Patent
Moon et al.

(10) Patent No.: US 11,974,972 B1
(45) Date of Patent: May 7, 2024

(54) ANTI-MYCOBACTERIAL DRUGS

(71) Applicants: Joong Ho Moon, Weston, FL (US); Michelle Miranda, Miami, FL (US)

(72) Inventors: Joong Ho Moon, Weston, FL (US); Michelle Miranda, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/388,696

(22) Filed: Nov. 10, 2023

Related U.S. Application Data

(62) Division of application No. 17/854,360, filed on Jun. 30, 2022, now Pat. No. 11,857,521.

(51) Int. Cl.

| | | |
|---|---|---|
| *A61K 8/43* | (2006.01) | |
| *A61K 31/133* | (2006.01) | |
| *A61K 31/155* | (2006.01) | |
| *A61K 31/17* | (2006.01) | |
| *A61K 31/277* | (2006.01) | |
| *A61K 31/4409* | (2006.01) | |
| *A61K 31/47* | (2006.01) | |
| *A61K 31/496* | (2006.01) | |
| *A61K 31/4965* | (2006.01) | |
| *A61K 31/498* | (2006.01) | |
| *A61K 31/5377* | (2006.01) | |
| *A61P 31/04* | (2006.01) | |
| *A61P 31/06* | (2006.01) | |
| *C07C 279/12* | (2006.01) | |
| *C07D 295/215* | (2006.01) | |
| *C08G 65/00* | (2006.01) | |
| *C08G 71/02* | (2006.01) | |

(52) U.S. Cl.
CPC ............ *A61K 31/17* (2013.01); *A61K 31/133* (2013.01); *A61K 31/277* (2013.01); *A61K 31/4409* (2013.01); *A61K 31/47* (2013.01); *A61K 31/496* (2013.01); *A61K 31/4965* (2013.01); *A61K 31/498* (2013.01); *A61K 31/5377* (2013.01); *A61P 31/06* (2018.01); *C07C 279/12* (2013.01); *C07D 295/215* (2013.01); *C08G 65/00* (2013.01); *C08G 71/02* (2013.01); *C07C 2601/16* (2017.05)

(58) Field of Classification Search
CPC ........ A61P 31/04; A61P 31/06; A61K 31/155; A61K 8/43; C07D 295/215
See application file for complete search history.

(56) References Cited

U.S. PATENT DOCUMENTS 10,017,462 B1  7/2018  Moon et al.

OTHER PUBLICATIONS

ACS Sprig 2022 Posters, "Mechanism studies of antimicrobial poly(guanylurea) 8K against *Mycobacterium smegmatis*," Mar. 22, 2022, 2 pages (https://scs.digitellinc.com/acs/live/22/).
Ballinger, Elaine et al. "Opposing reactions in coenzyme A metabolism sensitize *Mycobacterium tuberculosis* to enzyme inhibition." Science 363(6426): 1-9, (Year: 2019).
Bass, Rosemary et al. "Synthesis and Biological Evaluation of Amidinourea and Triazine Congeners as Inhibitors of MDA-MB-231 Human Breast Cancer Cell Proliferation." ChemMedChem 12(4):288-291, (Year: 2017).
Fortun, Solène and Schmitzer, Andreea R. "The chemistry of biguanides: from synthetic routes to applications in organic chemistry." Canadian Journal of Chemistry 98(6):251-260, (Year: 2020).
Kagermeier, Nicole et al. "Dimeric carbamoylguanidine-type histamine H2 receptor ligants: A new class of potent and selective agonists." Bioorganic & Medicinal Chemistry 23(14):3957-3969, (Year: 2015).
Kathuria, Deepika et al. "Biguanides: Species with versatile therapeutic applications." European Journal of Medicinal Chemistry 219, pp. 1-39, (Year: 2021).
Ottavi, Samantha et al. "In Vitro and In Vivo Inhibition of the Mycobacterium tuberculosis Phosphopantetheinyl Transferase PptT by Amidinoureas." Journal of Medical Chemistry 65(3):1996-2022, (Year: 2022).
Yu, Chunlei et al. "A Guanidinium-Rich Polymer for Efficient Cytosolic Delivery of Native Proteins." Biochonjugate Chemistry 30(2):413-417, (Year: 2019).

*Primary Examiner* — Jeffrey S Lundgren
*Assistant Examiner* — Chris E Simmons
(74) *Attorney, Agent, or Firm* — SALIWANCHIK, LLOYD & EISENSCHENK

(57) ABSTRACT

The subject invention provides oligo(carbamoylated guanidine)s (OCGs) having fast and selective mycobactericidal effects via disruption of the mycobacterial membrane potential. OCGs also potentiates bedaquiline, an oxidative phosphorylation-targeting anti-TB drug. The combination of OCG and anti-TB drug can be used as an effective therapy for treating tuberculosis.

20 Claims, 13 Drawing Sheets

Specification includes a Sequence Listing.

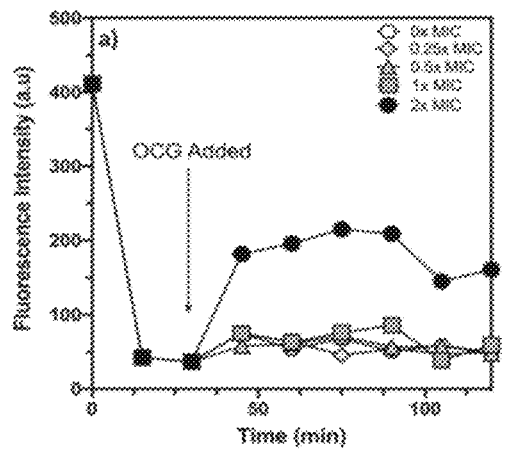 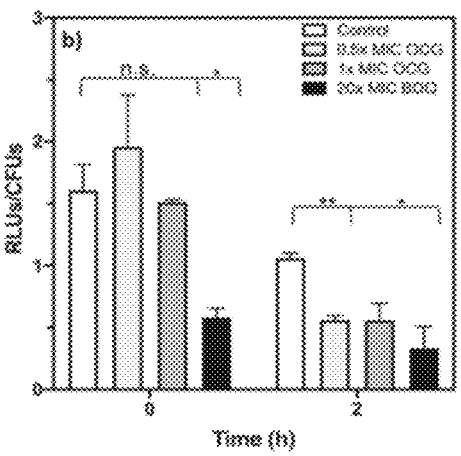
FIG. 13A　　　　　　　　FIG. 13B
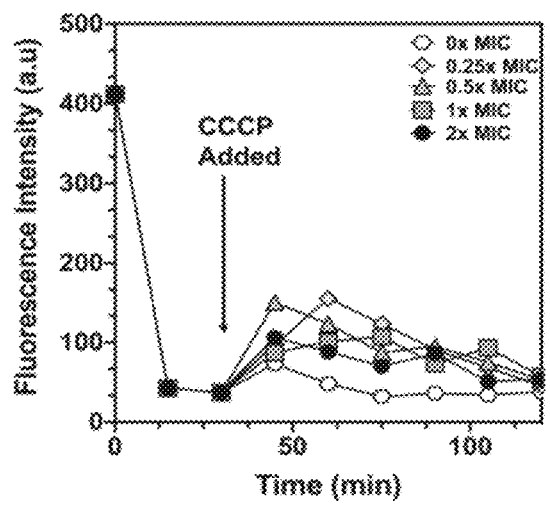 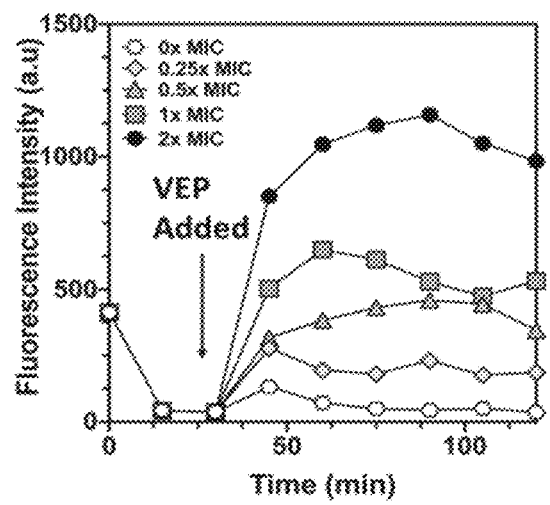
FIG. 14

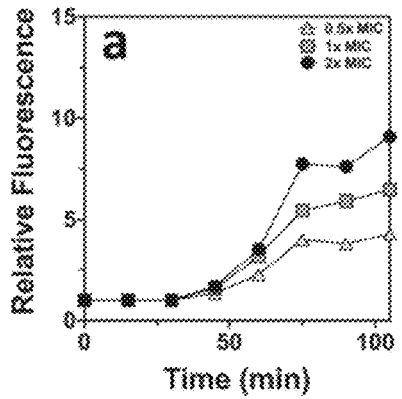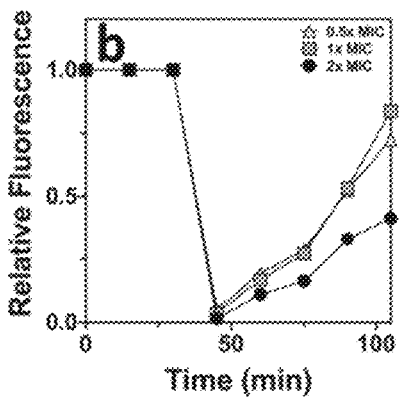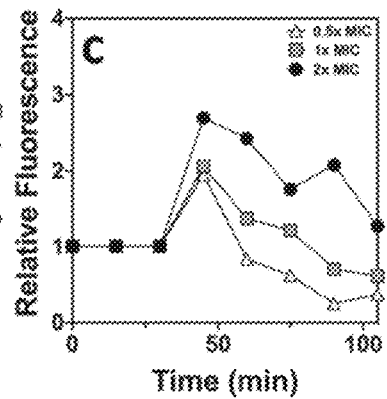
FIG. 15A                FIG. 15B                FIG. 15C
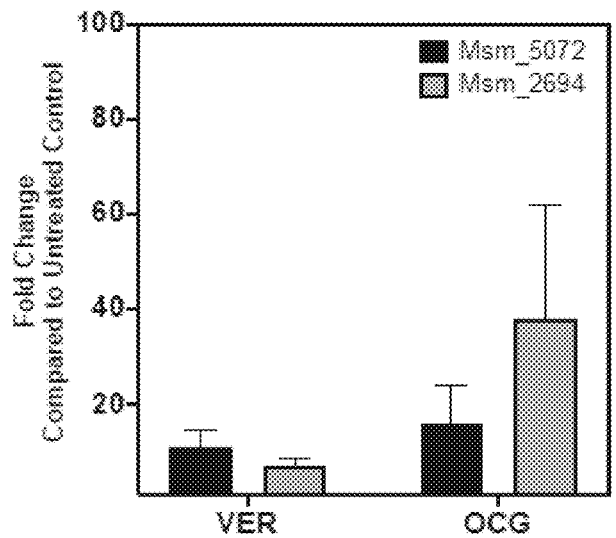
FIG. 16

SEQUENCE LISTING

```
Sequence total quantity: 4
SEQ ID NO: 1            moltype = DNA  length = 20
FEATURE                 Location/Qualifiers
misc_feature            1..20
                        note = primer
source                  1..20
                        mol_type = other DNA
                        organism = synthetic construct
SEQUENCE: 1
accttttcct cgacatggtg                                               20

SEQ ID NO: 2            moltype = DNA  length = 20
FEATURE                 Location/Qualifiers
misc_feature            1..20
                        note = primer
source                  1..20
                        mol_type = other DNA
                        organism = synthetic construct
SEQUENCE: 2
tcgtaggaca gaccctcgat                                               20

SEQ ID NO: 3            moltype = DNA  length = 18
FEATURE                 Location/Qualifiers
misc_feature            1..18
                        note = primer
source                  1..18
                        mol_type = other DNA
                        organism = synthetic construct
SEQUENCE: 3
gaggtgattg gcgacgtg                                                 18

SEQ ID NO: 4            moltype = DNA  length = 20
FEATURE                 Location/Qualifiers
misc_feature            1..20
                        note = primer
source                  1..20
                        mol_type = other DNA
                        organism = synthetic construct
SEQUENCE: 4
cgaaagtggt acgtcgagtg                                               20
```

ANTI-MYCOBACTERIAL DRUGS

CROSS-REFERENCE TO A RELATED APPLICATION

This application is a divisional application of U.S. Ser. No. 17/854,360, filed Jun. 30, 2022, now U.S. Pat. No. 11,857,521, which is hereby incorporated by reference herein in its entirety.

SEQUENCE LISTING

The Sequence Listing for this application is labeled "SeqList-22Nov23.xml" which was created on Nov. 22, 2023, and is 6,090 bytes. The Sequence Listing is incorporated herein by reference in its entirety.

BACKGROUND OF INVENTION

Tuberculosis (TB) is a deadly infectious disease caused by *Mycobacterium tuberculosis* (Mtb). The current TB treatment regimen is lengthy (i.e., 4-9 months) and rigorous (i.e., the daily dose of a combination of four drugs) due to difficulties associated with multidrug resistance (MDR) and nongrowing Mtb. Because most anti-TB drugs were developed to act on replicating cells, slow or nongrowing cells (persisters) are especially hard to target by using traditional strategies. Therefore, current efforts have focused on developing new drugs and drug combinations that act on unconventional targets to efficiently kill the subpopulation of Mtb to shorten the treatment period to less than two months.

Targeting the bacterial membrane has gained recent attention as a promising strategy to overcome MDR and eradicate dormant bacteria cells. An energized membrane is essential for the survival of both replicating and non-replicating organisms, because a substantial portion of cellular proteins responsible of vital processes are located in the membrane. Therefore, disturbing the membrane would lead to disruption of these essential functions, and seriously impede the bacteria from acquiring resistance or quickly lead to death. Broad-spectrum antimicrobial peptides (AMPs) and their synthetic mimics are a promising class of antibiotics owing to their unique bactericidal mechanism. By carefully balancing the hydrophobicity and charge density, AMPs selectively induce disruption of the bacterial membranes over mammalian cells. Although a promising approach, AMPs' lack of enzyme stability and selectivity to specific microbes has limited AMPs to primarily topical uses in clinical applications.

While most AMPs and AMP mimics exhibit relatively high efficiency against Gram-positive and -negative bacteria, a limited number of AMPs and AMP mimics shows good mycobacterial selectivity with high efficacy (i.e., ubiquitin and ubiquitin derivatives). Compared to other bacteria, the mycobacterial envelope is rigid, waxy, and less negatively charged, making the ionic interaction and the diffusion of positively charged AMPs and AMP mimics inefficient.

Therefore, there is a need to design and develop compounds such as AMP mimics with a high emphasis on a careful balancing on the positive charge and hydrophobicity of the pendant side chains to improve mycobacterial selectivity and antibacterial activity.

BRIEF SUMMARY

The subject invention provides compounds having antibacterial activities. Advantageously, the compounds of the subject invention exhibit high antimycobacterial selectivity over other microbes. The subject invention also provides compositions and methods for inhibiting bacteria, e.g., mycobacteria, and for treating a disease or condition caused by bacteria, e.g., mycobacteria.

In one embodiment, the subject invention provides an oligo(carbamoylated guanidine) (OCG) comprising the structure:

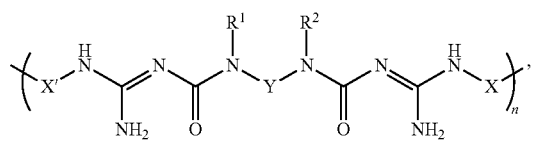

wherein n≥1; each X and X' is linear or cyclic alkylene, heteroatom interrupted alkylene, cycloalkylene, arylene, heteroarylene, or a combination thereof; each Y is linear or cyclic alkylene, heteroatom interrupted alkylene, cycloalkylene, arylene, heteroarylene, or a combination thereof; and $R^1$ and $R^2$ are independently, H, alkyl, substituted alkyl, heteroatom interrupted alkyl, aryl, substituted aryl, heteroarylene, or $R^1$ and $R^2$ are combined as an alkylene or heteroatom interrupted alkylene, wherein $R^1NYNR^2$ comprises a heterocycle.

In specific embodiments, each X and X' is an arylene, a cycloalkylene, or a heterocycle; and each Y is piperazine, oxyetylene, hexyl, oxydianiline, no diiodo or phenyl.

In one embodiment, OCGs of the subject invention comprises a neutral backbone and one or two cationic ends. In specific embodiments, the OCG of the subject invention comprising a neutral backbone and cationic ends has a structure of

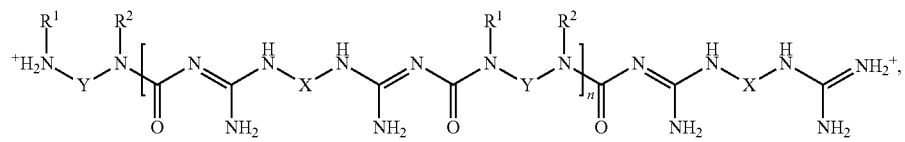

wherein n≥1; each X is linear or cyclic alkylene, heteroatom interrupted alkylene, cycloalkylene, arylene, heteroarylene, or a combination thereof; each Y is linear or cyclic alkylene, one or more heteroatom interrupted alkylene, cycloalkylene, arylene, heteroarylene, or a combination thereof, wherein the heteroatom is O, S, NH, or a combination thereof; and each $R^1$ and each $R^2$ are independently, H, substituted or unsubstituted linear, branched, or cyclic alkyl, one or more heteroatom interrupted substituted or unsubstituted linear branched or cyclic alkyl, wherein the heteroatom is O, S, NH or a combination thereof, unsubstituted or substituted aryl, unsubstituted or substituted heteroarylene, or $R^1$ and $R^2$ are combined as an alkylene or heteroatom interrupted alkylene, wherein $R^1NYNR^2$ comprises a heterocycle.

In one embodiment, the subject invention provides a pharmaceutical composition comprising an OCG or a salt thereof. The salt is, for example, the salt of acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid.

In one embodiment, the pharmaceutical composition further comprises an anti-TB drug selected from, for example, ciprofloxacin (CIP), clofazimine (CLZ), bedaquiline (BDQ), verapamil (VER), rifampin (RIF), ciprofloxacin (CIP), linezolid, isoniazid (INH), pyrazinamide (PZA), rifapentine (RPT), fluoroquinolones (e.g., moxifloxacin), and ethambutol. Preferably, the anti-TB drug is BDQ.

In one embodiment, the subject invention provides a method of treating a bacterial infection in a subject, the method comprising administering an effective amount of the pharmaceutical composition of the subject invention, preferably, the bacterial infection being a mycobacterial infection.

In certain embodiments, the administration is oral, topical, subcutaneously, intraperitoneally, intravenously, intramuscularly, or intradermally administration.

In specific embodiments, the subject invention provides a method of treating tuberculosis in a subject, the method comprising administering an effective amount of the pharmaceutical composition comprising the OCG of the subject invention and an anti-tuberculosis drug selected from CIP, CLZ, BDQ, VER, RIF, CIP, linezolid, INH, PZA, RPT, fluoroquinolones (e.g., moxifloxacin), and ethambutol.

In one embodiment, the subject invention also provides a method of inhibiting the growth of a *Mycobacterium*, the method comprising contacting the pharmaceutical composition of the subject invention with the *Mycobacterium*.

In one embodiment, the subject invention further provides a method of disrupting the mycobacterial membrane potential, the method comprising contacting the pharmaceutical composition of the subject invention with the *Mycobacterium*.

BRIEF DESCRIPTION OF DRAWINGS

FIG. 13A shows OCG effects on bioenergtics of Msm. Membrane depolarization effects of OCG measured using measured 5 μM DiSC$_3$(5) potentiometric dye. OCG at 2×MIC induces an immediate increase in fluorescence signals, indicating disruption of the membrane potentials. VER and CCCP at various concentrations were used as positive controls. Experiment was performed in triplicates (data from one representative experiment is shown for the clarity).

FIG. 13B shows OCG effects on bioenergtics of Msm. Intracellular quantification of ATP levels was performed using relative luminescence units (RLUs) normalized by colony forming units (CFUs) at time 0 h and 2 h after treatment of Msm cells. Experiment was performed in triplicates, and averaged ±standard deviation. *P<0.05, **P<0.01. n.s.: not significant. OCG showed immediate depolarization of the Dy, but depletion of ATP levels after 2 h of treatment.

FIG. 14 shows the membrane depolarization effect of verapamil against *M. smegmatis* using 5 μM DiSC$_3$(5).

FIG. 15A shows dye interaction of the tested compounds using 5 μM DiSC$_3$5 Dye and buffer (no cells) in the presence of verapamil.

FIG. 15B shows dye interaction of the tested compounds using 5 μM DiSC$_3$5 Dye and buffer (no cells) in the presence of CCCP.

FIG. 15C shows dye interaction of the tested compounds using 5 μM DiSC$_3$5 Dye and buffer (no cells) in the presence of OCG.

FIG. 16 shows transcriptional induction of membrane stress reporters in Msm by OCG in comparison to 2×MIC VER. Fold change was calculated in comparison to untreated control with 0.2% DMSO and sigA as housekeeping gene. OCG induces higher levels of overexpression of the genes related membrane stress sensing genes compared with VER, which was reported to disrupt the PMF.

BRIEF DESCRIPTION OF SEQUENCES

Figure 1A:
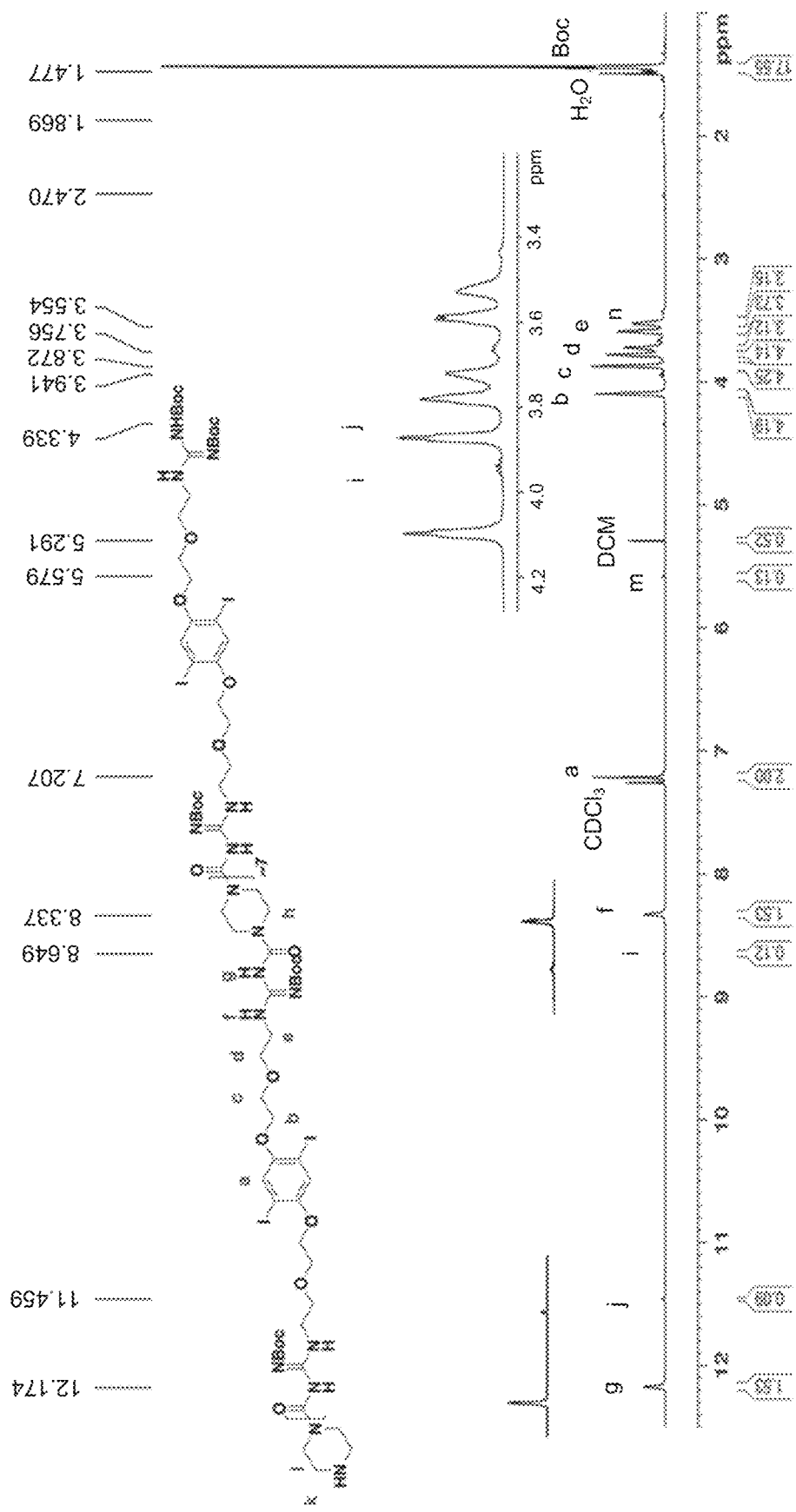
FIG. 1A shows NMR of Boc-protected OCG. $^1$H NMR (400 MHz, CDCl3, δ): 12.2 (s, 1H), 8.34 (t, 1H, J=4.8 Hz), 7.22 (s, 1H), 4.10 (t, 2H, J=4.6 Hz), 3.88 (t, 2H, J=4.6 Hz), 3.78 (t, 2H, J=5.1 Hz), 3.73 (br s, 2H), 3.60 (q, 2H, J=5.3 Hz, J=5.1 Hz), 3.53 (br s, 2H), 1.44 (s, 9H).

SEQ ID NO: 1 is a forward primer for MSMEG_5072 genes contemplated for use according to the subject invention.

SEQ ID NO: 2 is a reverse primer for MSMEG_5072 genes contemplated for use according to the subject invention.

SEQ ID NO: 3 is a forward primer for MSMEG_2694 genes contemplated for use according to the subject invention.

SEQ ID NO: 4 is a reverse primer for MSMEG_2694 genes contemplated for use according to the subject invention.

DETAILED DISCLOSURE

The subject invention provides compounds having antimycobacterial activities and high antimycobacterial selectivity over other microbes. The subject invention also provides compositions and methods for inhibiting mycobacteria and for treating a disease or condition caused by mycobacteria.

In one embodiment, the compounds are oligo(carbamoylated guanidine)s (OCGs), that are bactericidal, preferably, against mycobacteria. OCG exhibits fast, selective bactericidal effects without compromising the viability of host cells, a fast depolarization of the membrane potential (Δψ), and the overexpression of genes associated with the membrane stress sensing. Thus, OCG primarily acts on the membrane energetics by dissipating a component of the proton motive force (PMF) and depleting ATP production.

In certain embodiments, OCGs comprise a neutral backbone and one or two cationic ends. The neutral backbone comprises a plurality of carbamoylated guanidines, which provides a rigid structure. OCGs also contain H-bonding that can interact with bacterial cell membranes. In some embodiments, the neutral backbone of OCGs may be protonated, for example, after treatment by an acid, which leads to a positively charged backbone, for example, at guanidine(s).

In one embodiment, the carbamoylated guanidine comprises a structure of:

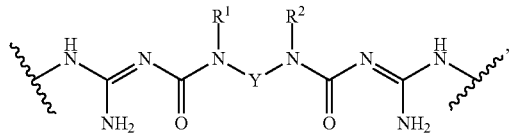

where Y is linear or cyclic alkylene, heteroatom interrupted alkylene, cycloalkylene, arylene, heteroarylene, or a combination thereof, wherein the heteroatom is O, S, NH, or a combination thereof; and $R^1$ and $R^2$ are independently, selected from, for example, H, substituted or unsubstituted linear, branched, or cyclic alkyl, one or more heteroatom interrupted substituted or unsubstituted linear branched or cyclic alkyl, wherein the heteroatom is O, S, NH or a combination thereof, unsubstituted or substituted aryl, unsubstituted or substituted heteroarylene, or $R^1$ and $R^2$ are combined as an alkylene or heteroatom interrupted alkylene, wherein $R^1NYNR^2$ comprises a heterocycle. Preferably, substituents are $C_1$ to $C_{20}$ alkyl, $C_1$ to $C_{20}$ alkoxy, hydroxyl, $C_1$ to $C_{20}$ acyl, $C_1$ to $C_{20}$ acyloxy, amino, $C_1$ to $C_{20}$ alkyl amino, $C_1$ to $C_{20}$ dialkylamino, $C_1$ to $C_{20}$ acylamino, $C_2$ to $C_{20}$ acylalkylamino, fluoro, chloro, bromo, iodo, mercapto, $C_1$ to $C_{20}$ alkylthio, $C_6$ to $C_{18}$ aryl, $C_6$ to $C_{18}$ aryloxy, $C_6$ to $C_{18}$ arylamino, $C_6$ to $C_{32}$ diarylamino, or $C_7$ to $C_{38}$ alkylarylamino.

In certain embodiments, OCGs of the subject invention comprise a general structure of

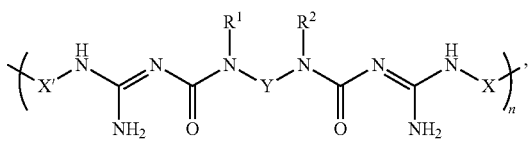

wherein n≥1, preferably, 3≤n≤100, more preferably, 3≤n≤50, most preferably, 3≤n≤20; X and X' are each independently linear or cyclic alkylene, heteroatom interrupted alkylene, cycloalkylene, arylene, heteroarylene, or a combination thereof; each Y is linear or cyclic alkylene, one or more heteroatom interrupted alkylene, cycloalkylene, arylene, heteroarylene, or a combination thereof, wherein the heteroatom is O, S, NH, or a combination thereof; and each $R^1$ and each $R^2$ are independently, H, substituted or unsubstituted linear, branched, or cyclic alkyl, one or more heteroatom interrupted substituted or unsubstituted linear branched or cyclic alkyl, wherein the heteroatom is O, S, NH or a combination thereof, unsubstituted or substituted aryl, unsubstituted or substituted heteroarylene, or $R^1$ and $R^2$ are combined as an alkylene or heteroatom interrupted alkylene, wherein $R^1NYNR^2$ comprises a heterocycle. Preferably, substituents are $C_1$ to $C_{20}$ alkyl, $C_1$ to $C_{20}$ alkoxy, hydroxyl, $C_1$ to $C_{20}$ acyl, $C_1$ to $C_{20}$ acyloxy, amino, $C_1$ to $C_{20}$ alkyl amino, $C_1$ to $C_{20}$ dialkylamino, $C_1$ to $C_{20}$ acylamino, $C_2$ to $C_{20}$ acylalkylamino, fluoro, chloro, bromo, iodo, mercapto, $C_1$ to $C_{20}$ alkylthio, $C_6$ to $C_{18}$ aryl, $C_6$ to $C_{18}$ aryloxy, $C_6$ to $C_{18}$ arylamino, $C_6$ to $C_{32}$ diarylamino, or $C_7$ to $C_{38}$ alkylarylamino.

In one embodiment, each Y is piperazine, oxyetylene, hexyl, oxydianiline, no diiodo or phenyl; and each X and X' comprises an arylene, a cycloalkylene, or a heterocycle. In specific embodiments, X and X' may be the same or different. In certain embodiments, X or X' may be absent.

In another embodiment, the OCG of the subject invention further comprises at least one tert-butyloxycarbonyl protecting group (BOC).

In some embodiments, the OCGs of the subject invention comprises a backbone having a structure of the following:

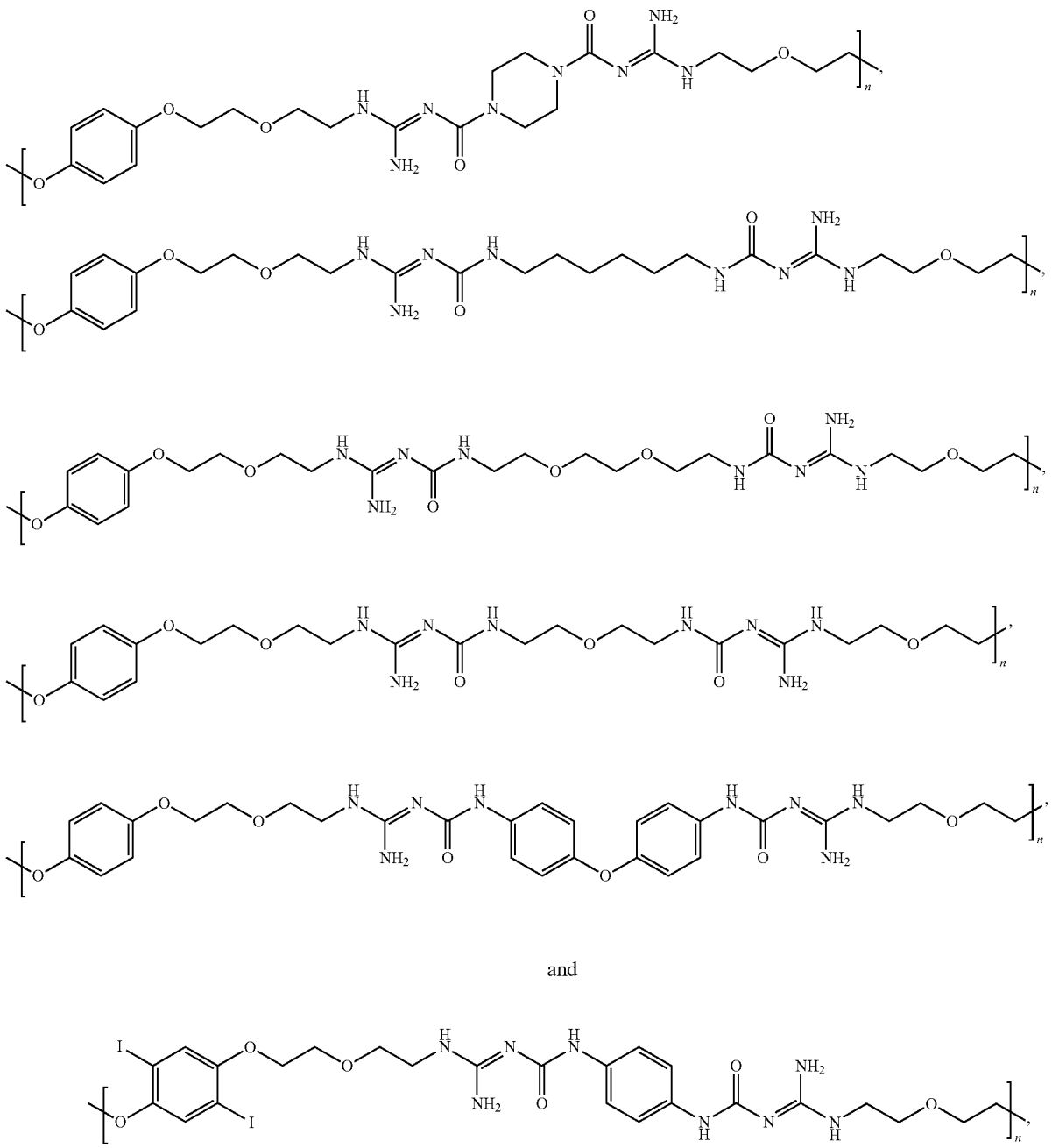

and wherein n≥1, preferably, 3≤n≤100, more preferably, 3≤n≤50, most preferably, 3≤n≤20.

In some embodiments, OCGs are oligo(carbomoylatedguanidine piperazine)s (OCG-Ps) synthesized by reacting piperazine with a monomer containing t-butyloxycarbonyl (Boc)-protected guanidine groups at the end of a short ethylene oxide side chains. The hydrophobic aryliodide units induce polymer chains to aggregate into nanoparticles (NPs) in bacteria culture medium. Piperazine creates rigidity between two guanylurea groups. The backbone rigidity and planarity is a synthetic mimic of AMPs, and play important roles in antimicrobial activity because of favorable membrane interaction.

In specific embodiments, the OCG of the subject invention comprising a neutral backbone and cationic ends has a structure of

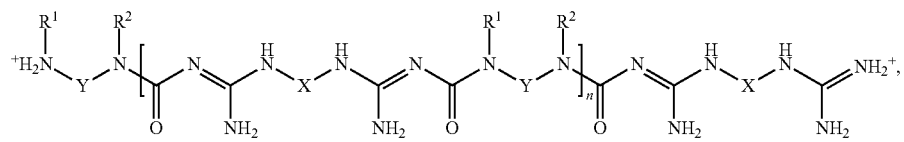

wherein n≥1, preferably, 3≤n≤100, more preferably, 3≤n≤50, most preferably, 3≤n≤20; each X is linear or cyclic alkylene, heteroatom interrupted alkylene, cycloalkylene, arylene, heteroarylene, or a combination thereof; each Y is linear or cyclic alkylene, one or more heteroatom interrupted alkylene, cycloalkylene, arylene, heteroarylene, or a combination thereof, wherein the heteroatom is O, S, NH, or a combination thereof; and each $R^1$ and each $R^2$ are independently, H, substituted or unsubstituted linear, branched, or cyclic alkyl, one or more heteroatom interrupted substituted or unsubstituted linear branched or cyclic alkyl, wherein the heteroatom is O, S, NH or a combination thereof, unsubstituted or substituted aryl, unsubstituted or substituted heteroarylene, or $R^1$ and $R^2$ are combined as an alkylene or heteroatom interrupted alkylene, wherein $R^1NYNR^2$ comprises a heterocycle. Preferably, substituents are $C_1$ to $C_{20}$ alkyl, $C_1$ to $C_{20}$ alkoxy, hydroxyl, $C_1$ to $C_{20}$ acyl, $C_1$ to $C_{20}$ acyloxy, amino, $C_1$ to $C_{20}$ alkyl amino, $C_1$ to $C_{20}$ dialkylamino, $C_1$ to $C_{20}$ acylamino, $C_2$ to $C_{20}$ acylalkylamino, fluoro, chloro, bromo, iodo, mercapto, $C_1$ to $C_{20}$ alkylthio, $C_6$ to $C_{18}$ aryl, $C_6$ to $C_{18}$ aryloxy, $C_6$ to $C_{18}$ arylamino, $C_6$ to $C_{32}$ diarylamino, or $C_7$ to $C_{38}$ alkylarylamino.

In a specific embodiment, the OCG of the subject invention has a structure of

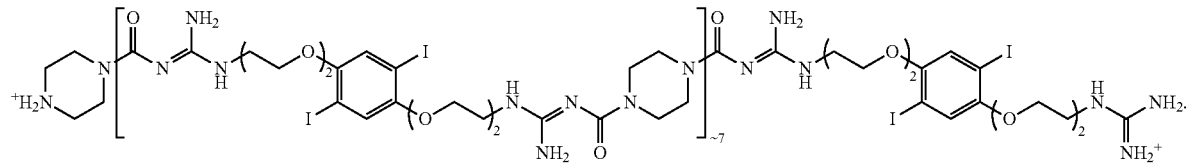

In one embodiment, the compounds have activity against bacterial pathogens, including both gram-positive and -negative bacteria, such as *Staphylococcus aureus* (a Gram-positive bacterium), methicillin-resistant *Staphylococcus aureus* (MRSA), and *Shigella flexneri* (a Gram-negative bacterium).

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram-positive bacteria" include cocci, nonsporulating rods, and sporulating rods. The genera of Gram-positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

In specific embodiments, the compounds have activity against mycobacteria, such as *Mycobacterium smegmatis* (Msm), *Mycobacterium kansasii, Mycobacterium abscessus* (Mab), *Mycobacterium avium* or *Mycobacterium tuberculosis* (Mtb). In a preferred embodiment, the compounds have activity against *M. tuberculosis*. The compounds also have activity against drug resistant bacterial pathogens, preferably, drug resistant mycobacteria, such as *M. tuberculosis*.

In one embodiment, the compounds inhibit the growth of bacterial pathogens by disrupting the membrane potential of the bacteria. Targeting membrane energetics is a promising approach to combat drug-resistant or latent mycobacterial infections as both replicating and dormant mycobacteria rely on a polarized membrane for their survival.

In one embodiment, the compounds are used as antibacterial drugs in antibacterial therapy. In a specific embodiment, the compounds are used in treatment of infectious diseases, preferably, tuberculosis. In some embodiments, the compounds can be used in combination with other drugs for infectious diseases to achieve synergistic effects for overcoming the resistance problem and reducing time required for treatment.

Specifically, OCGs of the subject invention potentiate anti-TB drugs that act on disrupting the membrane energetics (e.g., bedaquiline, an oxidative phosphorylation-targeting anti-TB drug). Accordingly, the combination of the OCG and one or more anti-TB drugs exhibits advantageous properties in disrupting the membrane potential and treating TB, for example, when compared to any OCG or anti-TB drugs alone. Thus, OCGs could be used as a new class of macromolecular anti-TB drugs or drug adjuvants.

In one embodiment, the current invention provides a pharmaceutical composition comprising a compound of the subject invention or a salt thereof. The composition further comprises a pharmaceutically acceptable carrier.

In certain embodiments, the pharmaceutical compositions can also include additional pharmaceutical active compounds know in the art. One or more anti-TB drugs may be included in the composition for treating TB. Such anti-TB drugs may include, but are not limited to, CIP, CLZ, BDQ, VER, RIF, CIP, linezolid, INH, PZA, RPT, fluoroquinolones (e.g., moxifloxacin), and ethambutol. One or more additional antibiotics may also be included in the composition. Moreover, the composition may be in a sterile form.

In specific embodiments, the antibiotics, include, for example, penicillins (such as penicillin G, penicillin V, ampicillin, amoxicillin, bacampicillin, carbenicillin, carbenicillin indanyl, ticarcillin, azlocillin, mezlocillin, methicillin, piperacillin, and the like), tetracyclines (such as chlortetracycline, oxytetracycline, methacycline, doxycycline, minocycline and the like), cephalosporins (such as cefadroxil, cephalexin, cephradine, cephalothin, cephapirin, cefazolin, cefaclor, cefamandole, cefonicid, cefoxitin, cefotetan, cefuroxime, cefuroxime axetil, cefmetazole, cefprozil, loracarbef, ceforanide, cefepime, cefoperazone, cefotaxime, ceftizoxime, ceftriaxone, ceftazidime, cefixime, cefpodoxime, ceftibuten, and the like), fluoroquinolones (e.g., levofloxacin), quinolones (such as nalidixic acid, cinoxacin, ciprofloxacin and norfloxacin and the like), lincomycins (e.g., clindamycin), macrolides (e.g., erythromycin, azithromycin), sulfones (e.g., dapsone), sulfonamides (e.g., sulfanilamide, sulfadiazine, sulfamethoxazole, sulfisoxazole, sulfacetamide, bactrim), lipopeptides (e.g., daptomycin), polypeptides (e.g., bacitracin), glycopeptides (e.g., vancomycin), aminoglycosides (e.g., streptomycin, gentamicin, tobramycin, amikacin, netilmicin, kanamycin, and the like), nitroimidazoles (e.g., metronidazole) and/or carbapenems (e.g., thienamycin).

Certain specific examples of antibiotics or anti-infectives according to the subject invention include, but are not limited to, ampicillin, doxycycline, cephalexin, ciprofloxacin, sulfacetamide, clindamycin, metronidazole, erythromycin, azithromycin, sulfamethoxazole, amoxicillin, oxytetracycline, tetracycline, streptomycin, dapsone, methicillin, penicillin, vancomycin, bacitracin, daptomycin, bactrim, tobramycin, p-aminobenzoic acid, diaminopyrimidine, β-lactam, β-lactamase inhibitor, glycopeptide, chloraphenicol, macrolide, corticosteroid, prostaglandin, ciprofloxacin, linomycin, clindamycin, spectinomycin, polymyxin B, colistin, isoniazid, rifampin, ethambutol, ethionamide, aminosalicylic acid, cycloserine, capreomycin, sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, terbinafine, levofloxacin and any combination thereof.

The OCGs, according to embodiments of the invention, can be provided separately or in combination with medicaments that are antibacterial, antiviral, antifungal, or any combination thereof. The medicaments can be formulated according to known methods for preparing pharmaceutically useful compositions. Such pharmaceutical compositions can be adapted for various forms of administration, such as, but not limited to, oral, parenteral, nasal, topical, and transdermal.

The OCGs can be provided as solutions, amorphous compounds, injectables, pills, inhalants, or in any other form for administration. The OCG compositions can include a pharmaceutically acceptable carrier or diluent. Formulations are described in a number of sources, which are well known and readily available to those skilled in the art. For example, *Remington's Pharmaceutical Science* (Martin E W [1995] Easton Pennsylvania, Mack Publishing Company, 19$^{th}$ ed.) describes formulations that can be used in connection with embodiments of the invention.

Formulations suitable for administration include, for example, aqueous sterile injection solutions, which may contain antioxidants, buffers, bacteriostats, and solutes, which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, or tablets of the compositions. It should be understood that in addition to the ingredients particularly mentioned above, the formulations of the subject invention can include other agents conventional in the art having regard to the type of formulation in question.

Pharmaceutically acceptable carriers used in formulations include, but are not limited to, inert diluents and vehicles such as: one or more excipients, buccal tablets, troches, capsules, elixirs, suspensions, syrups, wafers, and aerosol sprays. Tablets, troches, pills, capsules, and the like may, but do not necessarily, contain binders, such as gum tragacanth, acacia, corn starch or gelatin; excipients, such as dicalcium phosphate; a disintegrating agent, such as corn starch, potato starch, or alginic acid; a lubricant, such as magnesium stearate; a sweetening agent, such as sucrose, fructose, lactose or aspartame; flavoring agent, such as peppermint, oil of wintergreen, or cherry flavoring; a liquid carrier, such as a vegetable oil or a polyethylene glycol; and/or solid carriers; such as finely divided solids such as talc, clay, microcrystalline cellulose, silica, or alumina. Any material used in preparing the dosage form should be pharmaceutically acceptable and substantially non-toxic in the amounts employed. The dosage form may be a sustained-release preparation. Other dosage forms can include surfactants or other adjuvants. Liquid compositions for topical use can be applied from absorbent pads or be impregnated on bandages and other dressings. Thickeners, such as synthetic polymers, fatty acids, fatty acid salts and esters, fatty alcohols, modified celluloses or modified mineral materials, can be employed with liquid carriers.

Particularly, the carrier and/or diluent should not deteriorate the pharmacological potency of the active agent and the capability of the complex to be directed to a desired target within, or on, the animal body. Preferably, said carrier and/or diluent is/are selected from water, physiologically acceptable aqueous solutions containing salts and/or buffers and any other solution acceptable for administration to an animal. Such carriers and diluents are well known to a person skilled in this field and can be, for example, distilled water, de-ionized water, pure or ultrapure water, saline, phosphate-buffered saline (PBS), solutions containing usual buffers which are compatible with the other components of the drug targeting system etc.

The compounds may be in the free base form or in the form of an acid salt thereof. In some embodiment, compounds as described herein may be in the form of a pharmaceutically acceptable salt, which are known in the art (Berge S. M. et al., *J. Pharm. Sci.* (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). The acid salts can be generated with any pharmaceutically acceptable organic or inorganic acid.

Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Salts, as described herein, may be prepared by conventional processes known to a person skilled in the art, for example, and without limitation, by combining the free form with an organic acid or cation exchange from other salts. Those skilled in the art will appreciate that preparation of salts may occur in situ during isolation and purification of the compounds or preparation of salts may occur by separately reacting an isolated and purified compound.

In embodiments of the invention, the compounds may be in the form of a solvate. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol. In some embodiments of the invention, repeating units of the OCGs can be mixtures of isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience. The OCGs can be stereoregular or random polymers. The OCGs can be copolymers of various repeating units. The copolymers can be block copolymers, random copolymers, dendritic copolymers, or any other form of copolymers.

OCGs or pharmaceutical compositions for use as described herein may be administered by means of a medical device or appliance such as an implant, graft, prosthesis, stent, etc. Also, implants may be devised which are intended to contain and release such compounds or compositions. An example would be an implant made of a polymeric material adapted as a vehicle to release the OCGs over a period of time.

An "effective amount" of an OCG pharmaceutical composition includes a therapeutically effective amount or a prophylactically effective amount. A "therapeutically effective amount" refers to an amount effective, at dosages and for periods of time necessary, to achieve the desired therapeutic result. A therapeutically effective amount of an OCG formulation may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, a prophylactic dose is used in subjects prior to the disease, so that a prophylactically effective amount may be less than a therapeutically effective amount.

Dosage values may vary with the severity of the condition to be alleviated. For any particular subject, specific dosage regimens may be adjusted over time according to the individual need and the professional judgment of the person administering or supervising the administration of the compositions. Dosage ranges suggested herein are exemplary only and do not limit the dosage ranges that may be selected by medical practitioners. The amount of OCGs in the composition may vary according to factors such as the disease state, age, sex, and weight of the subject. Dosage regimens may be adjusted to provide the optimum therapeutic response.

In general, OCGs should be used without causing substantial toxicity. Toxicity of the OCGs can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions.

In one embodiment, the current invention provides a pharmaceutical composition for treating conditions involving bacterial infection, preferably tuberculosis. In one embodiment, the current invention provides methods for treating a patient with tuberculosis, comprising the administration of the pharmaceutical composition of the subject invention. The composition described herein has effective antibacterial activity.

As used herein, "infection" refers to the introduction and/or presence of a disease-causing, or pathogenic, organism into and/or in another organism, tissue or cell.

In one embodiment, the current invention also provides methods for treating an infection caused by a pathogen in a subject, comprising administering, to a subject in need of such treatment, an effective amount of the pharmaceutical composition comprising compound according to the subject invention. In one embodiment, the subject has been infected by a pathogen, e.g., a bacterium, preferably, *Mycobacterium*, such as Mtb.

In one embodiment, the method of treating tuberculosis comprises administering the composition of the subject invention to a subject having been diagnosed with tuberculosis, wherein the composition comprises an OCG, and/or an anti-TB drug.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The compositions can be administered to a subject by methods including, but not limited to, (i) administration through oral pathways, which administration includes administration in capsule, tablet, granule, spray, syrup, or other such forms; (ii) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (iii) administration topically, or as deemed appropriate by those of skill in the art for bringing the compound into contact with living tissue; and (iv) administration via controlled released formulations, depot formulations, and infusion pump delivery.

In specific embodiments, the compounds may be administered in the range of from 0.01 mg/kg body weight to 1 g/kg body weight, preferably, 1 mg/kg to 500 mg/kg body weight, more preferably, 50 mg/kg to 500 mg/kg body weight.

In one embodiment, the subject invention provides a method of inhibiting the growth of a pathogen such as a bacterium, the method comprising contacting the compound or the composition of the subject invention with the pathogen, or adding the compound or the composition of the subject invention to the medium comprising the pathogen.

Furthermore, it would be understood by those skilled in the art that the methods described in the present invention would not only apply to treatment in a subject, but could be applied to cell cultures, organs, tissues, or individual cells in vivo or in vitro, including immortalized cells isolated or derived from a subject.

In one embodiment, the subject invention provides a method for disrupting the membrane potential of a pathogen such as a bacterium, the method comprising contacting the compound or the composition of the subject invention with the pathogen, or adding the compound or the composition of the subject invention to the medium comprising the pathogen.

In one embodiment, the subject invention provides a method for disrupting the mycobacterial membrane potential, the method comprising contacting the compound or the composition of the subject invention with the mycobacteria, or adding the compound or the composition of the subject invention to the medium comprising the mycobacteria.

In a specific embodiment, the composition comprises an OCG, and/or an anti-TB drug.

The present invention also provides kits comprising the compounds and/or pharmaceutical compositions as described herein. The kits may further be used in the methods described herein. The kits may also include at least one reagent and/or instruction for their use. Moreover, the kits may include one or more containers filled with one or more compounds and/or pharmaceutical composition described in the present invention.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

As used herein, n is intended to include $\geq 1$, $\geq 2$, $\geq 3$, $\geq 4$, $\geq 5$, $\geq 6$, $\geq 7$, $\geq 8$, $\geq 9$, $\geq 10$, $\geq 11$, $\geq 12$, $\geq 13$, $\geq 14$, $\geq 15$, $\geq 16$, $\geq 17$, $\geq 18$, $\geq 19$, $\geq 20$, $\geq 21$, $\geq 22$, $\geq 23$, $\geq 24$, $\geq 25$, $\geq 26$, $\geq 27$, $\geq 28$, $\geq 29$, $\geq 30$, $\geq 31$, $\geq 32$, $\geq 33$, $\geq 34$, $\geq 35$, $\geq 36$, $\geq 37$, $\geq 38$, $\geq 39$, $\geq 40$, $\geq 41$, $\geq 42$, $\geq 43$, $\geq 44$, $\geq 45$, $\geq 46$, $\geq 47$, $\geq 48$, $\geq 49$, $\geq 50$, $\geq 51$, $\geq 52$, $\geq 53$, $\geq 54$, $\geq 55$, $\geq 56$, $\geq 57$, $\geq 58$, $\geq 59$, $\geq 60$, $\geq 61$, $\geq 62$, $\geq 63$, $\geq 64$, $\geq 65$, $\geq 66$, $\geq 67$, $\geq 68$, $\geq 69$, $\geq 70$, $\geq 71$, $\geq 72$, $\geq 73$, $\geq 74$, $\geq 75$, $\geq 76$, $\geq 77$, $\geq 78$, $\geq 79$, $\geq 80$, $\geq 81$, $\geq 82$, $\geq 83$, $\geq 84$, $\geq 85$, $\geq 86$, $\geq 87$, $\geq 88$, $\geq 89$, $\geq 90$, $\geq 91$, $\geq 92$, $\geq 93$, $\geq 94$, $\geq 95$, $\geq 96$, $\geq 97$, $\geq 98$, $\geq 99$, and $\geq 100$.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

EXAMPLES

Materials and Methods
Materials

Boc-protected monomer was synthesized. Trifluoroacetic acid (TFA) (Fisher Scientific, 99%), anhydrous tetrahydrofuran (THF) (Fisher Scientific), dichloromethane (DCM) (Fisher Scientific), anhydrous potassium carbonate ($K_2CO_3$) (Fisher Scientific), diethyl ether (Fisher Scientific), Deuterated solvents (Cambridge Isotope Laboratories), ethyl acetate (Fisher Scientific), dimethylformamide (DMF) (Fisher Scientific), and dimethyl sulfoxide (DMSO) (Fisher Scientific) were used as received. Piperazine (Acros, 98%) was purified by recrystallization from methanol. Milli-Q water with a resistivity of >18 MΩ·cm was obtained from an in-line Millipore RiOs/Origin water purification system.

Characterization $^1$H Nuclear magnetic resonance (NMR) spectra were obtained using a 400 MHz Avance Bruker NMR spectrometer. Chemical shifts were reported in parts per million (ppm) on the δ scale. Deuterated solvents chloroform-d (CDCl$_3$) or dimethyl sufoxide-d$_6$ (DMSO-d$_6$) were used as reference solvents; CDCl$_3$ (δ=7.26 ppm) for the Boc-protected product and DMSO-d$_6$ (δ=2.50 ppm) for the Boc-free product.

The number average molecular weight of the Boc-protected polymer was confirmed via gel permeation chromatography (GPC) against polystyrene standards using a Shimadzu high performance liquid chromatography (HPLC) system at a flow rate of 1.0 mL/min with 2 tandem PLgel 5 μM MIXED-D columns operating at 40° C. and SPD-20A ultraviolet visible (UV-Vis) as the detector.

The pKa of oligo(carbamoylated guanidine) (OCG) was determined via pH titration. A concentrated solution of OCG in DMSO was diluted to 2 mM in 1 mL of an acidified (pH~2.5) solution of 100 mM NaCl. The pH was measured using a Mettler Toledo in Lab Ultra-Micro pH Probe. The acidified solution was titrated at 5 μL increments of 25 mM NaOH. The pH readings were recorded from pH~2.5-11. After plotting ΔpH/Δvolume of NaOH, the two points where the largest change in pH occurred were found. The median volume between the two maxima was identified as the point where pH=pKa. Solution of 100 mM NaCl served as control. Experiment was performed in triplicates.

Synthesis of OCG

Briefly, Boc-protected guanidine containing diiodo (0.02 mmol) and piperazine (0.02 mmol) monomers were added in a 4 mL amber vial at a 1:1 mole equivalent. A catalytic amount of K$_2$CO$_3$ and 400 μL of THF was subsequently added to the monomers. The vial was closed tightly, and the reaction was left to stir overnight at 70° C. The resulting viscous solution was filtered through glass wool to remove K$_2$CO$_3$ and the filtrate was purified by precipitation twice in diethyl ether and once in methanol. Polymer molecular weight was confirmed via GPC and chemical structure via NMR.

Deprotected OCG

The white powder of Boc-protected product (10 mg) was dissolved in 2 mL DCM. Then 1 mL of TFA was added and left to stir overnight resulting in the deprotected product and dried in vacuo. The crude product was dissolved in minimum amount of DMF and precipitated in diethyl ether twice and lastly in ethyl acetate. The product was collected by decanting, and successively dried by high vacuum. The white powder was collected and dissolved in DMSO for future testing. Chemical structure was confirmed via NMR.

Minimum Inhibitory Concentration (MIC) and Time-Kill Assay

MIC was determined by broth microdilution method according to Clinical and Laboratory Standards Institute (CLSI) guidelines. *M. smegmatis* mc$^2$ 155 cells (ATCC 700084) were initially grown for 24 h in BD Difco 7H9 medium (0.2% glycerol and 0.05% Tween 80) and supplemented with 1% ADN (0.05% albumin, 0.02% dextrose, 0.0085% NaCl). Then cells were inoculated and grown to late log-phase in 7H9 medium with 0.2% glycerol (Fisher Scientific) and 0.05% Tween 80 (VWR).

Other microorganisms were grown from a single colony in 5 mL of media, where Yeast extract-Peptone-Dextrose (YPD) medium (Sigma Aldrich) was used to grow *Candida albicans* (ATCC 10231). *Escherichia coli* (ATTC 8739), and *Staphylococcus aureus* (ATCC 6538) were grown in Luria Broth (LB) medium (US Biological), and *Burkholderia cepacia* (ATCC 2516), and *Pseudomonas aeruginosa* (ATCC 15442) were grown in Nutrient Broth (NB) medium (Difco).

Cell suspensions were allowed to grow to late-log phase at 37° C. with shaking at 210 rpm overnight. *M. smegmatis* in LB was supplemented with 0.2% glycerol and 0.05% Tween 80 and grown overnight to late-log phase. *M. bovis* BCG (ATCC 35734), and *M. abscessus* (S and R) (ATCC 19977) with luminescent reporter were incubated in T25 flasks (TPP) at 37° C., in 5% CO$_2$ static for 2-3 days and 5-7 days, respectively. The optical density (OD$_{600}$) was adjusted for final concentration of $10^5$ CFU well$^{-1}$ for bacterial cells, and $10^3$ CFU well$^{-1}$ for *C. albicans*. Polymer solution and controls were prepared in the respective media and serially diluted two-fold in a clear round bottom 96-well microtiter plate (Cell treat, 229590), followed by the addition of 50 μL of the cell suspension. Ciprofloxacin was used as positive control for *E. coli, M. smegmatis*, and *S. aureus*, and amphotericin B was used as a positive control for *C. albicans*. Positive control for *M. bovis* BCG was kanamycin and for *M. abscessus* was amikacin. Negative control included 50 μL of cell suspension and 50 μL of 2% DMSO media. Plates were incubated statically at 37° C. for 48 h for *M. smegmatis,* 20 h for Gram-positive and -negative bacteria, and 30° C. for 20 h for yeast, before the adding 10 μL of 0.02% resazurin dye. After addition of the dye and further incubation time (19 h for *M. smegmatis,* 4 h for other microorganisms), fluorescence was measure 540/590 nm (excitation/emission) on a BioTek Synergy H1 plate reader after further incubation period. For *M. bovis* BCG, and *M. abcessus* (S and R) they were incubated for 3 days, and luminescence was read. Assays included two technical replicates and were repeated at least three independent experiments.

For Time-Kill assay, *M. smegmatis* mc$^2$ 155 was cultured as previously described in the MIC assay. Cells were adjusted to OD$_{600}$ 0.01. OCG at 12, 24 and 48 μM were prepared in 7H9 supplemented with 0.2% glycerol and 0.05% Tween 80. A two-fold dilution of the polymer solutions was performed by the addition of 50 μL of subculture suspension for a final volume of 100 μL, and final polymer concentrations of 24 μM, 12 μM and 6 μM in a clear 96-well microtiter plate. Negative control was prepared by adding 50 μL of 2% DMSO in 7H9 medium, and 50 μL of bacterial cells. Aliquots of each sample were serially diluted 10-fold in 1× Phosphate-buffered saline buffer (PBS) and plated in LB Agar plates at 4 h, 8 h, 12 h and 24 h. After incubating the plates at 37° C. for six days, the colonies were counted. Experiment included duplicates and performed at least three independent times.

Checkerboard Assay

The bacterial cell suspension for the synergistic studies were prepared as described in the MIC assay. Drug samples were prepared in 7H9 medium with 2% DMSO and serially diluted two-fold horizontally in a clear 96-well microtiter plate. OCG was serially diluted two-fold and added vertically to the wells. Lastly, 100 μL of bacterial cell suspension was added in the wells for a total volume of 200 μL and a final concentration of 1% DMSO in each well. The plates were incubated statically at 37° C. After 48 h incubation, 20 µL of 0.02% resazurin was added to each well. Fluorescence intensity 540/590 nm (excitation/emission) was measured after 19 h incubation on a BioTek Synergy H1 plate reader. Experiment was performed at least three independent times, but one representative experiment was shown. Fractional Inhibitory Concentration Index value was calculated for each experiment using the following equation:

$$\sum FIC = FIC_A + FIC_B = \left(\left(\frac{MIC_{A+B}}{MIC_A}\right) + \left(\frac{MIC_{A+B}}{MIC_B}\right)\right)$$

where $MIC_A$ is the Minimum Inhibitory Concentration of compound A, $MIC_B$ is the Minimum Inhibitory Concentration of compound B and $MIC_{A+B}$ is the Minimum Inhibitory Concentration of the combination of compound A and compound B.

Ethidium Bromide Accumulation Assay

M. smegmatis cells were incubated to log-phase in 7H9 at 37° C. The bacterial cell suspension was centrifuged at 10000×g for 5 min at 25° C., washed twice, and resuspended in 1× PBS with 0.05% Tween 80 (PBST). The $OD_{600}$ was adjusted to 0.2. OCG, and bedaquiline (BDQ) were prepared in 1×PBST and 50 µL pipetted into the wells of a black-sided 96-well microtiter plate (Thermo Scientific Nunc, 165305). The bacterial suspension was pipetted for a ratio one-to-one of cell to polymer for a final volume of 100 µL in each well and a final concentration of 1% DMSO. Ethidium bromide (EtBr) dye at 2.5 µM was added as the fluorescent probe. EtBr can accumulate inside the cell and intercalate with nucleic acids leading to an increase of fluorescence signal. This assay can give insight on the intracellular accumulation of the dye, since EtBr is a small molecule that can enter the cell and is a substrate of efflux pumps. The accumulation can be attributed to outer membrane damage or due to inhibition of efflux pumps. The experiment was repeated at least three independent times and standard deviation depicted by error bars.

Outer Membrane Permeability Assay

M. smegmatis cells were grown as previously mentioned. Cells were centrifuged at 4000×g for 2 min at 25° C., washed and resuspended in 1×PBS. The resulting cells were adjusted to $OD_{600}$ 0.4. OCG was prepared at 1×MIC, 2×MIC and 4×MIC in 1×PBS buffer with 2% DMSO and 50 µL was added to an optical bottom black-sided 96-well microtiter plate (ThermoFisher, 165305). The bacterial cell suspension with 5 µM Sytox green dye, a membrane impermeable dye, was added to the wells for a final volume of 100 µL in each well. Wells not containing polymer were used as the negative control, and cells lysed in a bead Beater as positive control. The fluorescence at 485/590 nm (excitation/emission) was monitor every 5 min for 2 h at 37° C. on a BioTek Synergy plate reader. Experiments were performed in triplicates.

Similarly, outer membrane permeability assay using 10 µM N-Phenyl-2-naphthylamine in 4% acetone was used as a non-fluorescent dye that upon hydrophobic interaction, it emits fluorescence signal. Cells were grown to mid-log phase ($OD_{600}$=0.5), centrifuged at 4000×g for 2 min at 25° C., washed and resuspended in 5 mM HEPES buffer, pH 7.2. Compounds were made in HEPES buffer and 50 µL was added to an optical bottom black-sided 96-well microtiter plate. Then 50 µL of 40 µM NPN solution and 100 µL of cell suspension were added to the plate. Fluorescence was measured at 350/400 nm (excitation/emission) for 1 h. Experiments were performed in triplicates.

Membrane Depolarization Assay

Bacterial cells were grown to late log-phase in 7H9. Cells were centrifuged at 3000×g for 5 min at 25° C., washed twice and resuspended in 10 mL of 5 mM HEPES buffer, pH 7.2 supplemented with 1 mM glucose. $OD_{600}$ of the cells was then adjusted to 0.4. The cell suspension was treated with 1 µM of the potentiometric probe 3,3'-Dipropylthiadicarbocyanine Iodide ($DiSC_3(5)$) was added. It was incubated at 37° C., and monitored the quenching of $DiSC_3(5)$ dye in the presence of M. smegmatis cells for 30 min. In a black-sided 96-well microtiter plate, polymer solution was added to the plate and serially diluted two-fold in 50 mM HEPES buffer supplemented with 1 mM glucose and 2% DMSO for a final volume of 50 µL per well and 1% DMSO. After 30 min of quenching $DiSC_3(5)$, 50 µL of the bacterial suspension with dye was added to the polymer-containing wells. Wells without polymer were used as negative controls, verapamil and CCCP were used as positive control. Fluorescence was recorded 590/635 nm (excitation/emission) for 1 h every 10 min on a BioTek Synergy H1 plate reader. Assay was performed at least three independent experiments.

Quantification of Intracellular ATP Levels

Bacterial cells were grown to mid-log phase ($OD_{600}$=0.5) and treated with 2.4 BDQ µg/mL, OCG (6 and 3 µg/mL) or 0.2% DMSO. Aliquots of treated samples were separated for CFU analysis and for cell lysing at shortly after treatment (time=0 h) and after 2 h of treatment. Treated cultures for 2 h were incubated at 37° C., with shake (210 rpm). The aliquot separated for CFU analysis was serially diluted 10-fold in PBS and plated in LB agar plates to count the colonies after static incubation for six-days at 37° C. The aliquot separated for cell lysing was transferred to a o-ring-containing screw-cap 2 mL microtubes (Fisher Scientific) with 0.1 mm zirconia/silica beads (Biospec). Cells were lysed in a bead beater for two 1 min intervals with ice-cooling in between. The cell lysates were added to a white-sided optical bottom 96-well plate (Thermo Scientific Nunc, 165306) and then 50 µL of BacTiter-Glo™ Cell Viability Assay (Promega) was added for a final volume of 100 µL in the wells. Luminescence was then shortly after recorded in a BioTek Synergy H1 plate reader. The relative luminescence units (RLUs) data was divided by the CFUs to normalize the ATP levels per treatment and presented as RLUs/CFUs.

Transmission Electron Microscopy

M. smegmatis $mc^2$ 155 was culture as previously described in the MIC assay. Cells at $OD_{600}$=1.6 were treated with 2×MIC of OCG for 1 h, 4 h and 24 h in 7H9 medium. After treatment period, 500 µL of the solution was centrifuge at 3000×g for 30 s at 25° C. The pellet was resuspended in 1 mL glutaraldehyde/cacodylate fixative solution and stored at −20° C. before imaging. Images were analyzed for significant morphological changes. The frequency of membrane ruffling, membrane delamination, cytosolic leakage, and cells that appeared hollowed (i.e., cell death) were counted and divided by the total cell number per frame. The percent of the observed cell envelope stress indicators was used for statistical analysis.

Real-Time Quantitative Reverse Transcription-PCR Assay

M. smegmatis WT cells were grown to mid-log cultures in 7H9 at 37° C. and treated with OCG and VEP for 1 h at 2×MIC. The bacterial cell suspension centrifuged at 40000×g for 5 min at 25° C. and resuspended in 1 mL guanidine thiocyanate (GTC) buffer. The cells were spun down at 12000×g for 5 min and resuspended in 750 µL of TRIzol reagent (Invitrogen), and added to 0.5 mL of 0.1 mm zirconia/silica beads. Cells were lysed in a bead beater for two 1 min intervals with incubation on ice between intervals. Afterwards, 200 µL of chloroform was added to the tube, mixed, and spun at 12000×g for 15 min. The aqueous layer was carefully removed to 500 µL of RNase-free ethanol and mixed. From the solution, 700 µL were loaded onto Rnease Kit (Qiagen) miniprep columns and spun at 10000×g for 1 min. The remainder of the solution was then loaded and spun. The column was washed with 700 µL of RW1 buffer and discarded. The column was then washed twice with 500 µL RPE buffer and spun as previously described. The column was transferred to a new tube to elute the sample using 30 µL of RNase-free water and spun.

To ensure there is DNA-free, the sample was treated using TURBO DNA-free kit (Ambion) where a 1 µL of DNase and 3.5 µL of 10× DNase Buffer were added to the 30 µL of RNA and incubated for 1 h at 37° C. Then 5 µL of DNase Inactivation reagent was added, incubated for 2 min at room temperature and spun down at 10000×g for 2 min. The supernatant was removed to a clean tube and stored at −80° C. The concentration of RNA was determined through a ThermoFisher multichannel NanoDrop and adjusted to 50 ng/mL for cDNA reaction. The cDNA reaction was performed using iScript cDNA synthesis kit (BioRad), where 14 µL of RNase-free water, 4 µL iScript buffer, 1 µL iScript Reverse Transcriptase, and 1 µL of 50 ng/mL RNA were added to react in the thermocycler.

Finally, the qRT-PCR reaction was performed by adding 5 µL of iTaq Sybr green (BioRad), 3 µL RNase-free $H_2O$, 0.5 µL forward primer, 0.5 µL reverse primer, 1 µL of cDNA, and added to the thermocycler. SigA was used as the housekeeping gene. Fold change calculations were made in comparison to untreated control. Assay was performed in triplicates with two independent experiments.

PCR Primers

Cytotoxicity

J774 (TIB-67) or Hep G2 (ATCC HB-8065) cells were seeded in a black-sided 384-well plate (~10,000 cells/well) in 24 µL of Dulbecco's Modified Eagle Medium (DMEM) and allowed to attach for 4 h at 37° C. under a humidified atmosphere of 5% $CO_2$ prior to sample treatment. In separate 384-well plate, OCG was tested by serially diluting two-fold with a final concentration of 4% DMSO using the liquid handling robot from Integra Biosciences. After addition of the samples, cells were incubated statically for 20 h prior to addition of 0.01% resazurin dye and incubated for an extra 4 h at 37° C. 2% Triton-X was used as positive control while media with 4% DMSO as negative control. Fluorescence was measured 540/590 nm (excitation/emission). Cell viability was determined relative to control wells. Assay was performed in duplicates with three independent experiments.

Example 1—Characterization and Cytotoxicity

Figure 1B:
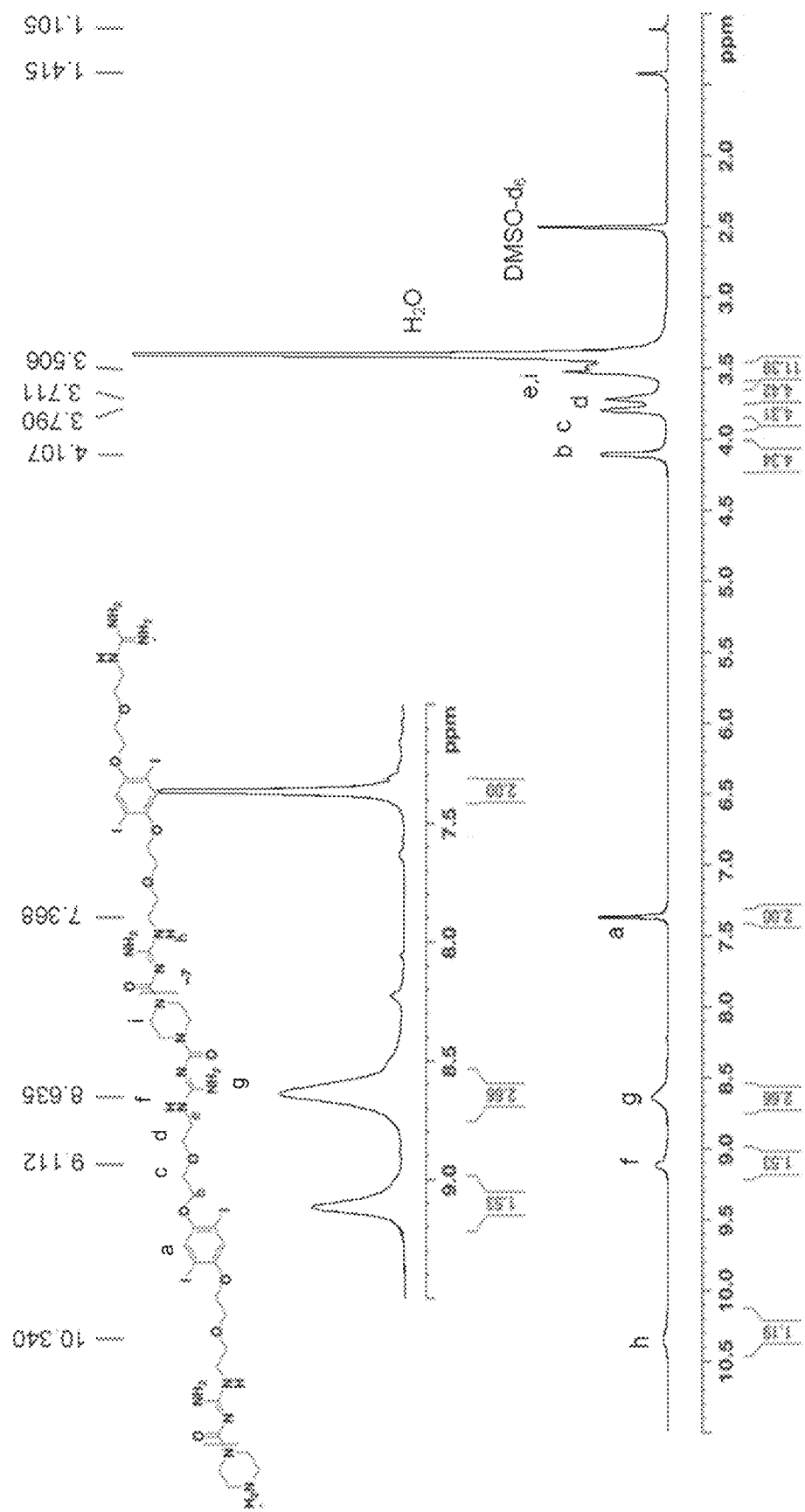
FIG. 1B shows NMR of Boc-deprotected OCG in acidic conditions. White fibrous solid (85% yield). 1H NMR (400 MHz, DMSO-d6, δ): 10.3 (s, 1H), 9.1 (s, 1H), 8.61 (s, 2H), 7.4 (s, 2H), 4.1 (s, 4H), 3.8 (s, 4H), 3.7 (s, 4H), 3.5 (m, 11H).
Figure 2:
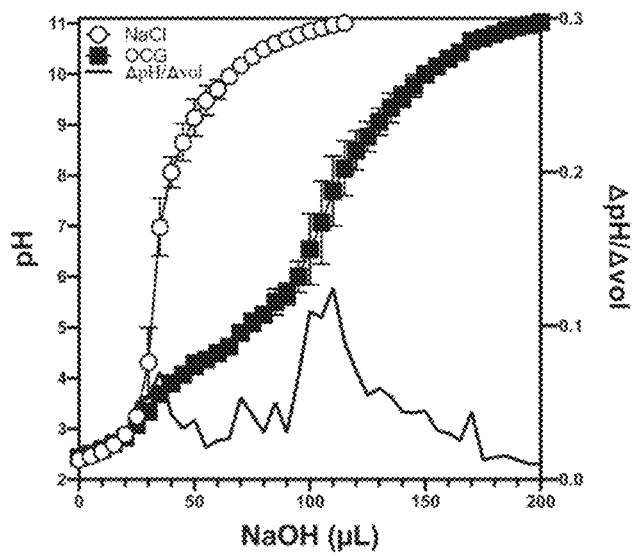
FIG. 2 shows the polymer characterization. Determination of pka via pH titration curve using 2 mM OCG in 100 mM NaCl using 25 mM NaOH from pH 2.5 to 11. Data shows the mean of three independent experiments ±standard deviation.
Figure 3:
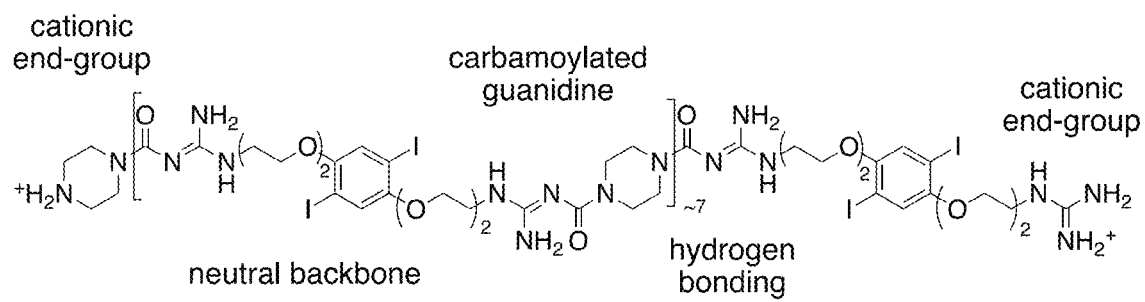
FIG. 3 shows the chemical structure of an OCG.
Figure 4A:
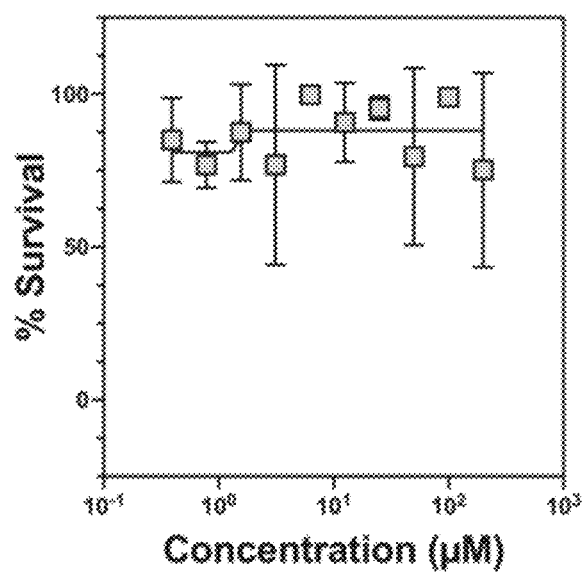
FIG. 4A shows the toxicity of OCG on J774, murine macrophage cell lines. It shows that OCG is non-toxic to J774.
Figure 4B:
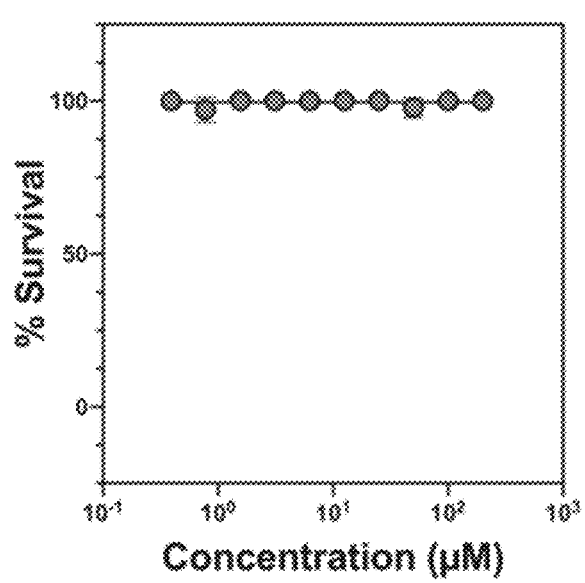
FIG. 4B shows the toxicity of OCG on cell lines HepG2, hepatic cell line. It shows that OCG is non-toxic to HepG2.

OCG was synthesized and the average molecular weight of OCG was confirmed by both gel permeation chromatography (GPC) and proton nuclear magnetic resonance (H NMR) spectroscopy (FIGS. 1A-1B), indicating that the number of CG repeating unit is ~7. The pKa of OCG was determined as ~5 (FIG. 2), indicating that the OCG backbone is neutral in the physiological condition while the two chain end groups (i.e., secondary amine and guanidine, FIG. 3) are positively charged. Nonhemolytic OCG showed no indication of decreased cell viability of a murine macrophage (i.e., J774) and a human liver carcinoma cell line (i.e., Hep G2) up to 200 µg/mL (FIGS. 4A-4B).

Example 2—Minimum Inhibitory Concentration

Minimum inhibitory concentrations (MICs) of OCG confirmed the mycobacterial selectivity over other microbes including Gram-positive (*Staphylococcus aureus*), Gram-negative (*Escherichia coli, Burkholderia cepacia*, and *Pseudomonas aeruginosa*), and a fungus (*Candida albicans*) (Table 2).

TABLE 1

Sequences of PCR primers used to test the cell envelope stress in Msm.

| Genes | Product | Forward Primers | Reverse Primers |
|---|---|---|---|
| MSMEG_5072 | extracytoplasmic function alternative sigma factor | 5'- ACC TTT TCC TCG ACA TGG TG -'3 (SEQ ID NO: 1) | 5'- TCG TAG GAC AGA CCC TCG AT -'3 (SEQ ID NO: 2) |
| MSMEG_2694 | transcriptional regulator, xenobiotic-response element (XRE) family protein | 5'- GAG GTG ATT GGC GAC GTG-'3 (SEQ ID NO: 3) | 5'- CGA AAG TGG TAC GTC GAG TG-'3 (SEQ ID NO: 4) |

TABLE 2

Selectivity of OCG against standard disinfectant strains of various microorganisms.

| Microorganisms MIC$_{90}$ (µg/mL) | | | | | |
|---|---|---|---|---|---|
| Mycobacteria | Gram-positive | Gram-negative | | | Fungi |
| Msm [a] | Sa [b] | Ec [c] | Bc [d] | Pa [e] | Ca [f] |
| 6 | 50 | >200 | >200 | >200 | >200 |

Strains tested
[a] *M. smegmatis* mc 155.
[b] *S. aureus* ATCC 6538.
[c] *E. coli* ATCC 8739.
[d] *B. cepacia* ATCC 2516.
[e] *P. aureginosa* ATCC 15442.
[f] *C. albicans* ATCC 10231.

Interestingly, the MIC against Msm cultured in Luria broth (LB) was increased ~four times compared with that of the same Msm cultured in 7H9 medium (Table 3). Because the morphology could be affected by the culturing conditions, the ~four-fold MIC change could be related to an altered interaction of OCG with the corresponding envelope.

TABLE 3

MIC values of OCG against different Mycobacteria
Mycobacteria MIC$_{90}$ (µg/mL)

| Msm [a] | Msm [b] | BCG [c] | Mab S [d] | Mab R [e] |
|---|---|---|---|---|
| 6 | 25-50 | 25 | 65 | 188 |

Strains tested.
[a] Msm mc$^2$ 155 grown in 7H9 medium.
[b] Msm mc$^2$ 155 grown in LB.
[c] *M. bovis* BCG grown in 7H9.
[d] Mab 3690 S grown in MHB medium.
[d] Mab 3690 R grown in MHB medium To further investigate how chemical compositions of the envelope influences the functions of OCG, MICs of two different morphotypes of *Mycobacterium abscessus* (Mab) treated with OCG were measured (Table 3). Mab can form both morphologically smooth (S) and rough (R) colonies when the surface-associated glycopeptidolipids (GPLs) are present and absent, respectively, in the cell envelope. The di- or triglycosylated GPLs are considered to screen the hydrophobic mycobacterial mycolic acids, thus the membranes of Mab(S) are relatively less hydrophobic than those of Mab (R). A ~three-fold increase in the MIC against the R morphotype suggests that GPLs might affect the antimycobacterial activity of OCG. Indeed, OCG generally shows better MICs toward mycobacteria expressing high GPLs such as Msm and Mab(S) (Table 3).

Figure 5:
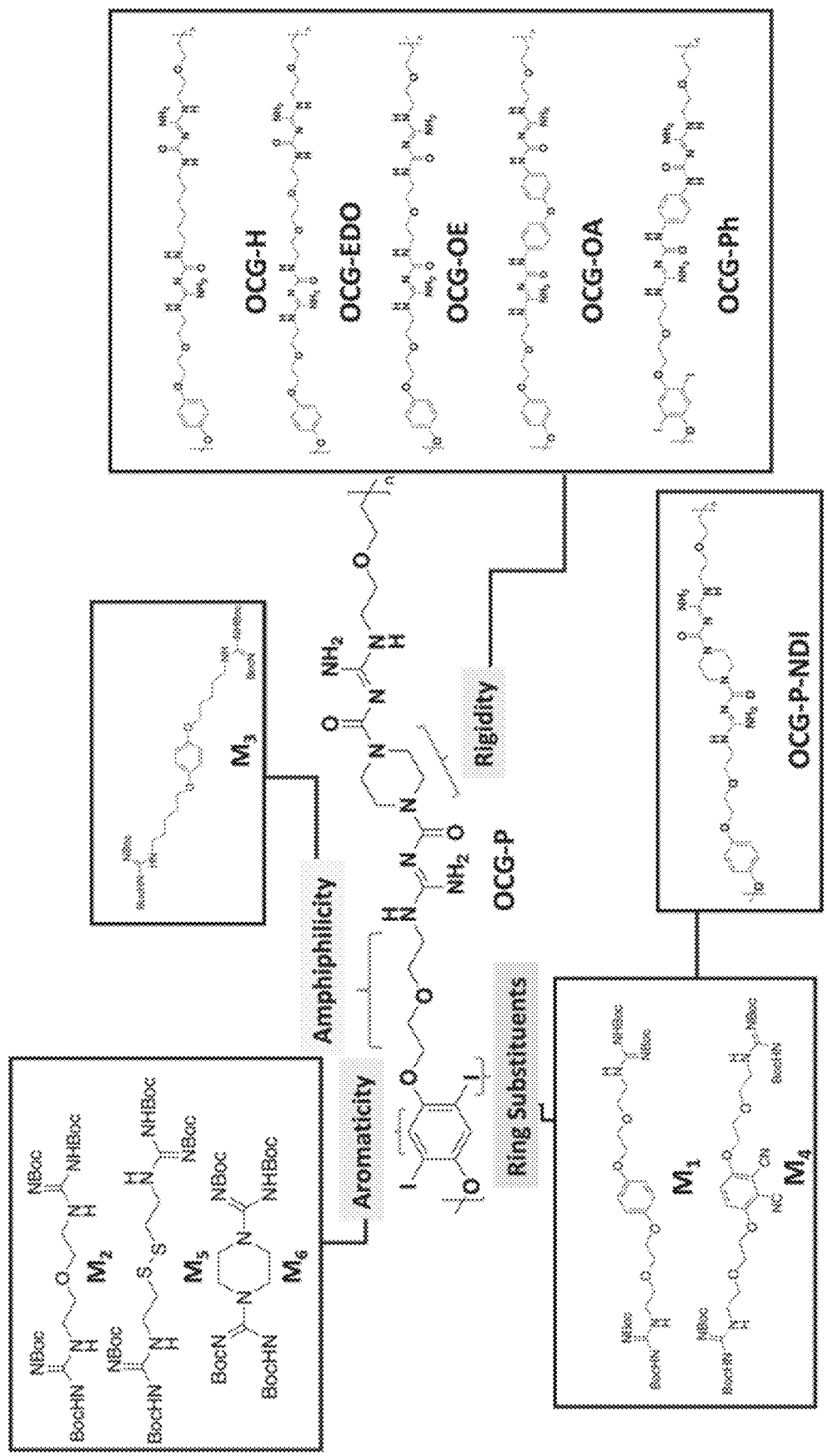
FIG. 5 shows different OCGs designs.

Different OCGs are shown in FIG. 5. MIC of OCGs against *M. smegmatis, S. aureus* and *E. coli* are shown in Table 4.

TABLE 4

Structure-Activity Relationship (SAR) of OCGs
Microorganisms MIC$_{90}$ (µg/mL)

| Oligomers OCGs | Mycobacteria Msm | Gram-positive Sau | Gram-negative Eco |
|---|---|---|---|
| P | 6 | 25 | >200 |
| P-NDI | 6 | >200 | >200 |
| H | 12.5 | 200 | >200 |
| OA | 6 | 25 | 200 |
| EDO | 6-12 | >200 | >200 |
| Ph | 6 | 50 | 200 |

P: Piperazine;
OE: oxyetylene;
H: hexyl;
OA: oxydianiline;
NDI: no diiodo;
Ph: phenyl

Example 3—Time-to-Kill Assay

Figure 6:
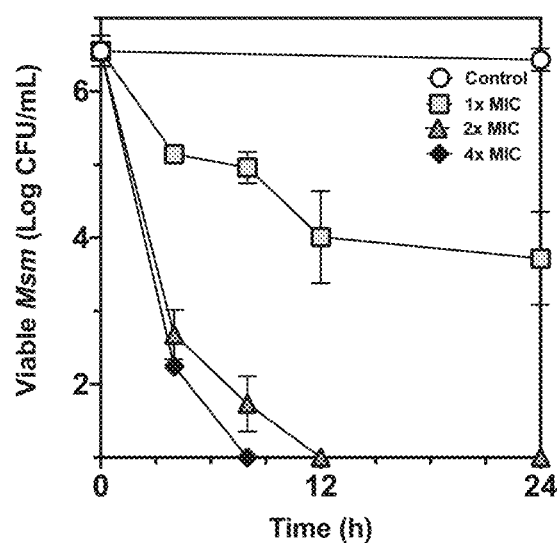
FIG. 6 shows the fast bactericidal activity of OCG. Within several hours of OCG treatment at 2×MIC, the number of viable Msm cells were exponentially decreased. Results were taken from three independent experiments with at least two technical replicates and averaged standard deviation.

The time-to-kill assay was conducted via colony forming unit (CFU) analysis at various concentrations of OCG to determine the minimal bactericidal concentration (MBC), which is defined as the lowest concentration to reduce bacterial viability by more than 99.9% with a concentration no more than 4×MIC. As shown in FIG. 6, the fast killing of Msm was observed within several hours of OCG treatments at 2×MIC or higher, indicating that OCG is bactericidal. Additionally, the bactericidal activity is fast-acting in comparison to anti-TB drugs including bedaquiline (BDQ), rifampicin (RIF), or verapamil (VER). The fast-acting bactericidal activity could be due to possible multidentate interaction of OCG to the membrane.

Example 4—Outer Membrane Assay

Figure 7:
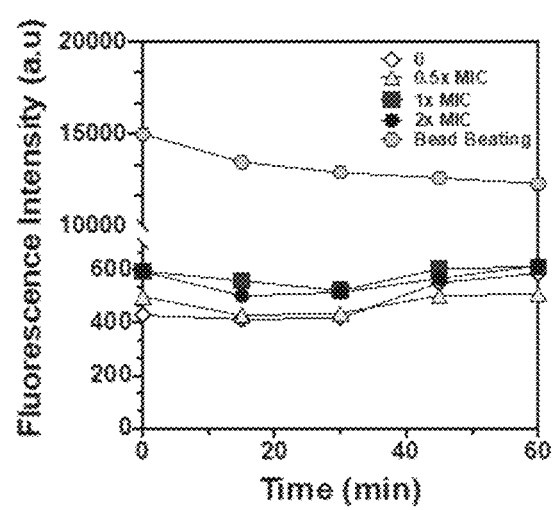
FIG. 7 shows the testing of the outer membrane permeability of OCG at 0.5×MIC, 1× MIC, and 2×MIC against *M. smegmatis* mc$^2$ 155. The fluorescence of 5 μM Sytox Green dye was read 485 nm/590 nm (ex,em) and monitored for 1 h. Cells lysed via bead beater were used as a positive control.
Figure 8:
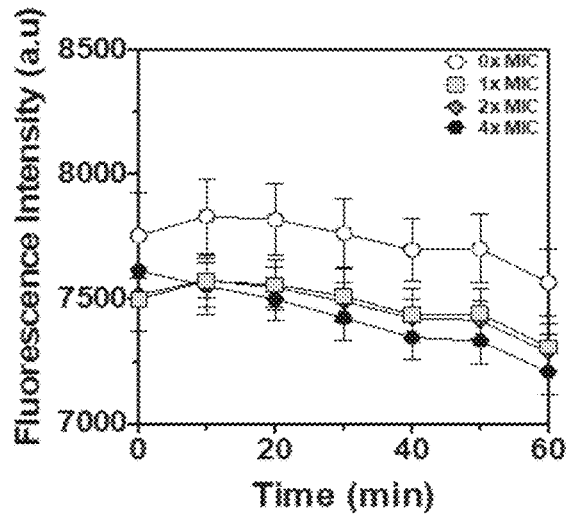
FIG. 8 shows the additional testing of the outer membrane permeability of OCG at 0.5× MIC, 1×MIC, 2×MIC and 4×MIC against *M. smegmatis* mc$^2$ 155 using 10 μM N-Phenyl-2-naphthylamine at 2% acetone was read 350 nm/400 nm (ex,em) and monitored for 1 h. Cells containing 4% acetone were used as negative control.

A membrane permeability assay using Sytox green dye was performed to examine whether the bactericidal effect is directly related to the disruption of membrane integrity. Fluorescence intensity of Sytox green increases when the membrane-impermeable dye intercalates into the intracellular nucleic acids upon diffusion through the damaged membranes. No fluorescence change was observed from Msm treated with OCG at 2×MIC for 1 h (FIG. 7). An additional assay commonly used for membrane damage was also conducted. Non-fluorescent hydrophobic N-phenyl-2-naphthylamine (NPN) becomes fluorescent upon interacting with damaged hydrophobic lipids in the membrane. Even after treating Msm with OCG at 4×MIC for 1 h, no fluorescence intensity increase was observed (FIG. 8). Both results indicated bactericidal effects of OCG may not be related to physical membrane damage.

Example 5—Transmission Electron Microscopy

Figure 9A:
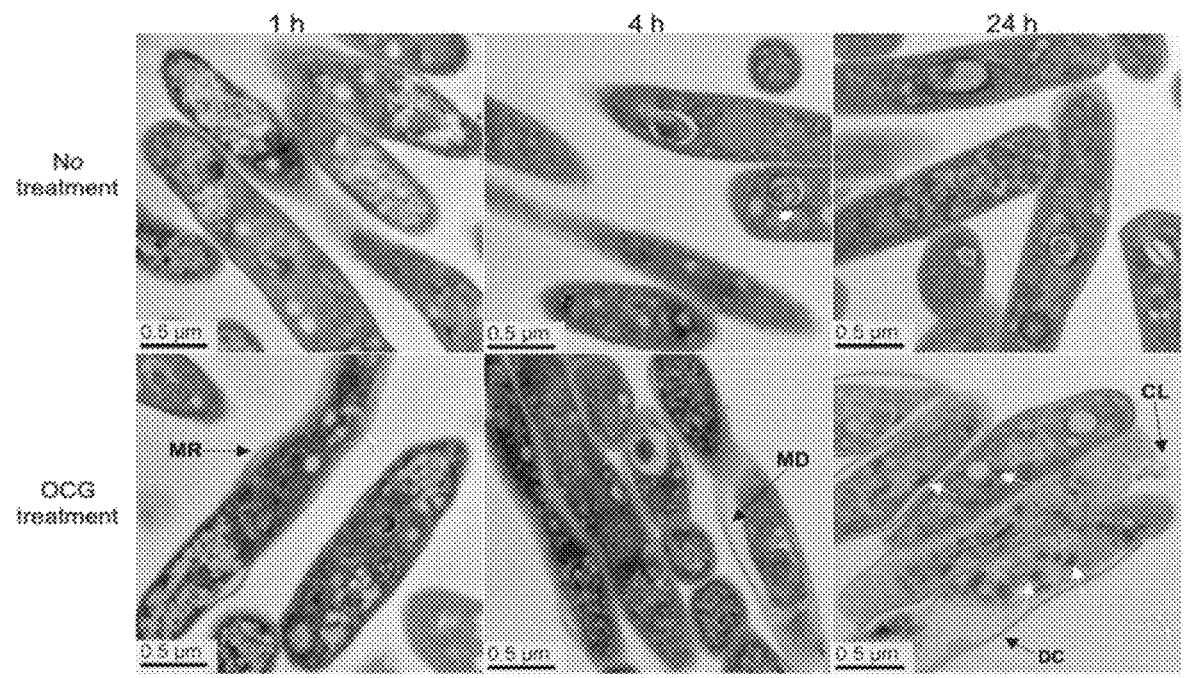
FIG. 9A shows the representative TEM micrographs of Msm cells after treatment with OCG at 2×MIC for 1, 4, and 24 hours, respectively. MR: membrane ruffling, MD: membrane delamination, CL: cytosolic leakage, and DC: dead cell.
Figure 9B:
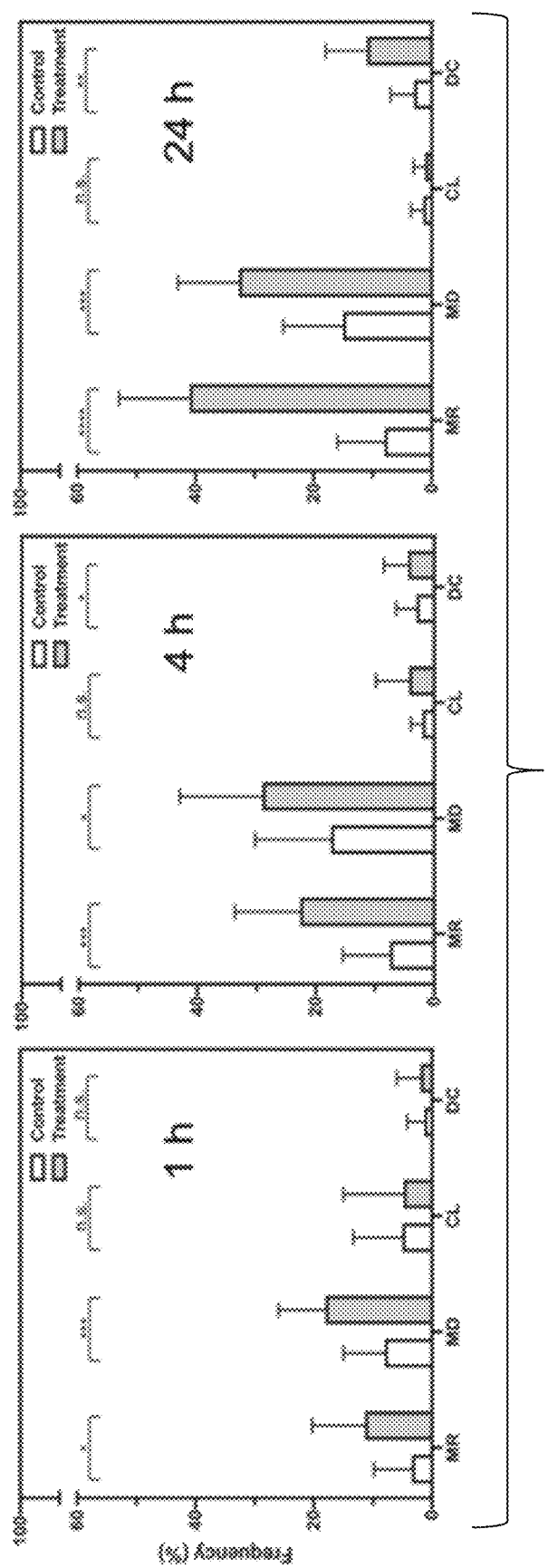
FIG. 9B shows that by counting the frequency of the specific morphological change in every image, statistical analysis of morphological changes induced by OCG was conducted. *P<0.01, P<0.001, *P<0.0001, ****P<0.00001. n.s.: not significant.
Figure 10:
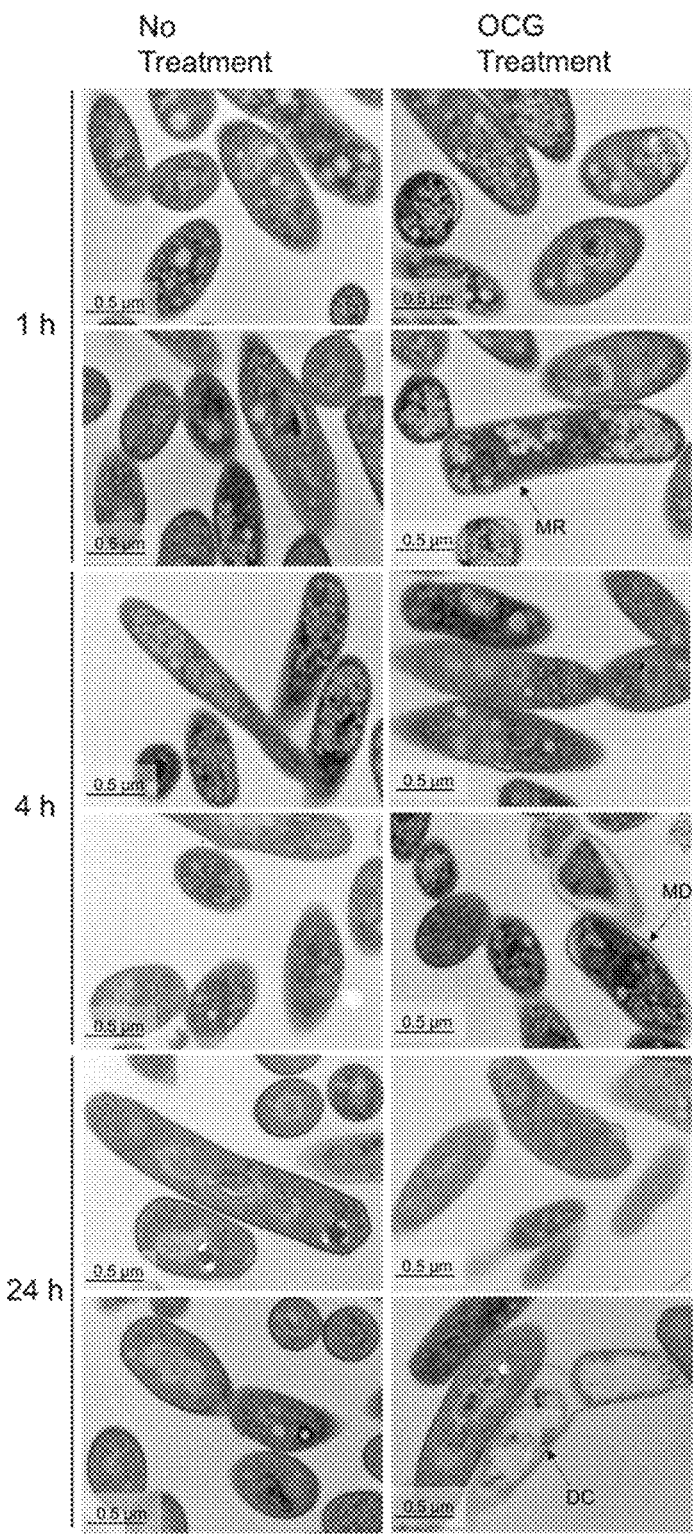
FIG. 10 shows the additional inset TEM micrographs with duplicates (vertically) of untreated Msm cells at 1 h, 4 h, and 24 h and treatment of OCG at 2×MIC for 1 h, 4 h, and 24 h. Each image is representative of the 25 images taken for each nontreated and treated period. Scale bars, 0.5 μm.

Transmission electron microscopic (TEM) images of Msm treated with OCG at 2×MIC for up to 24 h were collected and analyzed to examine the effects of OCG on the bacterial cell wall. After OCG incubation for 1, 4, and 24 hours, respectively, at 2×MIC, cells were fixed and stained for TEM imagining. As shown in FIGS. 9A-9B, typical morphologies, membranes, and cellular contents of intact Msm were observed from both treated and nontreated cells along with natural morphological changes (also in FIG. 10).

To warrant the objectivity of the image analysis, twenty-five images were taken per each treatment group, and each image was then analyzed by counting the frequency (%) of membrane ruffling (MR), membrane delamination (MD), cytosolic leakage (CL), and dead cell (DC) per total cells in each image. While no significant difference in the frequency of the cytosolic leakage was observed from both treated and non-treated cells up to 24 h incubation, signs of membrane stress including ruffling and delamination were observed starting from 1 h OCG treatment (FIG. 9B). An intact outer membrane was often observed from the dead cells, ruling out the damages on the membrane integrity as a bactericidal mode of action. Interestingly, increasing numbers of certain cytosolic aggregations (white arrows) were seen in 24 h OCG treated cells. The result suggests that those aggregation structures could be induced by internalized OCGs interacting with the cytosolic contents.

Example 6—Synergistic Studies

Although the antimicrobial effects of combining multiple drugs are hard to predict and interpret, any combination effects (e.g., synergistic, additive, or antagonistic) from combined drugs could provide a mechanistic insight. To evaluate drug potentiation effects of OCG, the checkerboard assay was conducted for selected anti-TB drugs, and the fractional inhibitory concentration indexes (FICIs) of the combinations were calculated.

Figure 11:
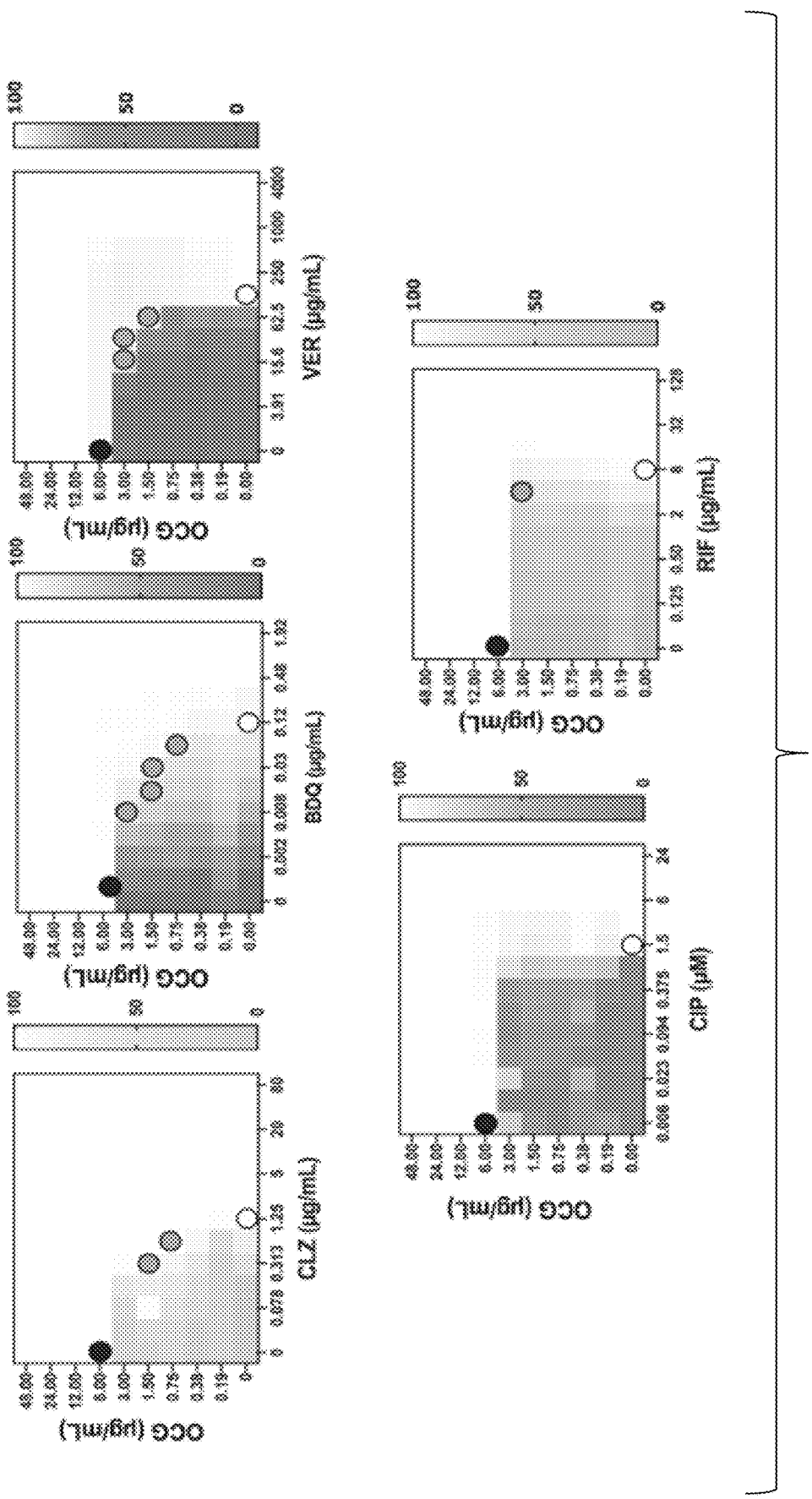
FIG. 11 shows the assessment of synergistic interactions between OCG, verapamil, and some anti-TB drugs. OCG was tested in combination with bedaquiline (BDQ), verapamil (VER), clofazimine (CLZ), ciprofloxacin (CIP) and rifampin (RIF) in checkerboard assay against *M. smegmatis*. The Minimum Inhibitory Concentration (MIC) value of OCG (6 μM) was denoted by a black circle, and white for the compounds tested against OCG: BDQ is 0.12 μg/mL, VER 250 μg/mL, CLZ 2.5 μg/mL, CIP 1.5 μM and RIF 8 μg/mL. The Fractional Inhibitory Concentration Index (FICI) values were calculated to be 0.38-0.5, 0.623-0.75, 0.50-0.75, 2, and 1-2 for BDQ, VER, CLZ, CIP and RIF, respectively. Synergy was observed in the combination with BDQ, but other PMF disruptors, CLZ and VER, showed some susceptibility in combination with OCG. Data was collected in three independent experiments, FICI values were calculated for each well, and represented by a FICI range. One representative experiment for each is shown.

Two sets of drugs were selected based on targeting 1) the membrane energetics [i.e., BDQ: adenosine triphosphate (ATP) synthase, clofazimine (CLZ): NADH dehydrogenase-2, VER: membrane energetics] and 2) intracellular processes [i.e., RIF: RNA polymerase and ciprofloxacin (CIP): DNA gyrase and topoisomerase IV]. As shown in FIG. 11, OCG exhibits the synergistic effects (i.e., FICI≤0.5) with BDQ and additive effects (i.e., 0.5<FICI≤1.0) with VER and CLZ. The synergistic effect of BDQ could be due to the possible disruption of a component of the proton motive force (PMF) by OCG, since ATP-synthase utilizes the PMF to produce ATP. Meanwhile, drugs acting on the intracellular targets show the indifferent effects (i.e., 1<FICI<2). These OCG-mediated potentiation and indifferent effects on the tested drugs imply that OCG possibly targets the membranes' energetics.

FICI values and interaction of OCG with some representative anti-tb drugs have been shown in Table 5.

TABLE 5

FICI values and interaction of OCG with some representative anti-TB drugs.

| Drug | Target | FICI | Interaction |
| --- | --- | --- | --- |
| Bedaquiline (BDQ) | $F_1/F_0$-ATP synthase | 0.38-0.5 | Synergy |
| Verapamil (VER) | Membrane energetics | 0.63-0.75 | Additive |
| Clofazimine (CLZ) | NADH dehydrogenase-2 | 0.5-0.75 | Additive |
| Ciprofloxacin (CIP) | DNA gyrase and topoisomerase IV | 2 | Additive |
| Rifampin (RIF) | RNA polymerase | 1-2 | Additive |

Example 7—Accumulation of Ethidium Bromide Assay

Figure 12A:
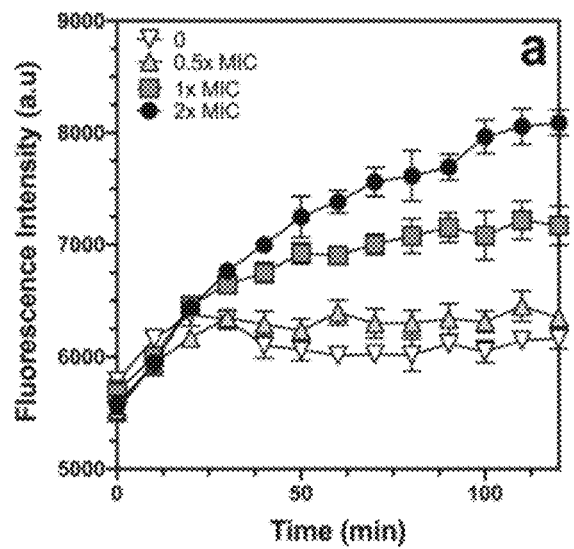
FIG. 12A shows ethidium Bromide Accumulation Assay. Intracellular accumulation assay of 2.5 μM ethidium bromide when treating *M. smegmatis* against OCG at 0.5×MIC, 1×MIC and 2×MIC. Fluorescence of ethidium bromide (ex. 530 nm, em. 585 nm) was monitored every 10 min for 2 h. Intracellular concentration of ethidium bromide was increased in a concentration-dependent matter for OCG. Experiment is shown in mean of triplicates ±standard deviation.
Figure 12B:
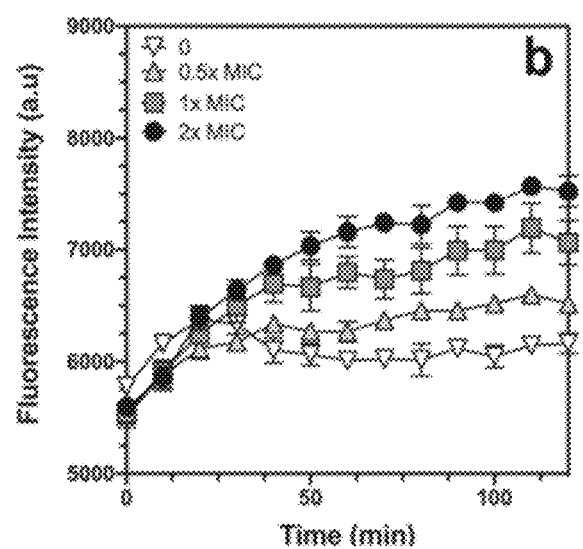
FIG. 12B shows ethidium Bromide Accumulation Assay. Intracellular accumulation assay of 2.5 μM ethidium bromide when treating *M. smegmatis* against BDQ at 0.5×MIC, 1×MIC and 2×MIC. Fluorescence of ethidium bromide (ex. 530 nm, em. 585 nm) was monitored every 10 min for 2 h. Intracellular concentration of ethidium bromide was increased in a concentration-dependent matter for BDQ. Experiment is shown in mean of triplicates ±standard deviation.

Efflux pumps draw energy from hydrolysis of ATP, ions, or protons. Therefore, disruption of these processes could lead to inhibition of efflux pumps. Ethidium bromide (EtBr), a fluorescent dye, is an efflux pumps' substrate and damages on the membrane directly or indirectly lead to the accumulation of EtBr. As shown in FIGS. 12A-12B, a concentration-dependent fluorescence increase was observed from both OCG- and BDQ-treated cells. Considering that OCG does not cause physical membrane damage, the increased fluorescent signals could be an indirect result of impaired functions of the efflux pumps. The dissipation of the PMF caused by BDQ indirectly damaged the efflux pumps, resulting in the accumulation of EtBr.

Example 8—Membrane Depolarization Assay

Selectivity is a critical requirement when developing novel therapeutics to minimize off-target risk towards mammalian cells or symbiotic bacteria. Dissipating the PMF is an appealing mechanism to combat TB. Although the collapse of the PMF itself is not bactericidal in most species, the survival of both growing and dormant Mtb necessitates a polarized membrane. PMF is composed of two main parameters: $\Delta \psi$ and $\Delta pH$, where the membrane potential ($\Delta \psi$) plays a greater role in mycobacteria. To measure the $\Delta \psi$ an assay using a potential-sensitive fluorescent dye [i.e., 3,3'-dipropylthiadicarbocyanine iodide, $DiSC_3(5)$] was conducted. As shown in FIGS. 13A-13B, the self-quenched dye in a hyperpolarized membrane was released to the solution (i.e., fluorescence increase) upon addition of OCG at 2×MIC, indicating that OCG disrupted $\Delta \psi$, similarly to the positive control, VER (FIGS. 13A-13B).

Meanwhile, cyanide m-chlorophenyl hydrazone (CCCP), a commonly used protonophore that collapses both of the components of the PMF did not exhibit concentration-dependent potential changes (FIGS. 15A-15C). This is largely due to the interference on the fluorescence signals of $DiSC_3$ (5) dye quenched by the ionophore.

Example 9—Real-Time Quantitative Reverse Transcription-Polymerase Chain Reaction Assay Because the disruption of the membrane potential induces a significant stress on the membranes, the genes associated with membrane stress sensing could be upregulated. A real-time quantitative reverse transcription-polymerase chain reaction (qRT-PCR) assay was conducted to study the regulation of MSMEG_5072 and MSMEG_2694 genes. These genes are orthologs responsible for cell envelope stress-sensing Phage shock protein (Psp) system of Mtb that CCCP has been shown to upregulate after treatment. As shown in FIG. 16, OCG treatment at 2×MIC for an hour induces a 10- and 50-fold times increased expression levels of MSMEG_5072 and MSMEG_2694 genes, respectively, compared to control Msm, confirming that the bactericidal properties of OCG are linked to the disruption of the PMF.

Thus, the results show that selective mycobactericidal activities of OCG are due to efficient dissipation of the membrane potential, a major component of the PMF, and depletion of intracellular ATP via selective interactions with the mycobacterial membranes. Compared with traditional TB drugs, OCG exhibit fast acting mycobactericidal effects presumably due to multidentate interactions of the amphiphilic CG group with mycobacterial cell membrane. Considering the design simplicity of OCG, unique targeting ability, and synergistic effects with existing TB drugs, OCG could contribute to the development of a novel class of anti-TB drug that efficiently combat deadly TB.

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A method of treating a bacterial infection in a subject, the method comprising administering an effective amount of a pharmaceutical composition comprising an oligo(carbamoylated guanidine) (OCG) comprising a general structure of:

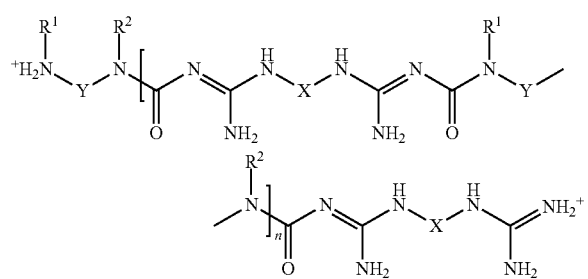

wherein n is an integer from 3 to 50;

X is an alkylene; a heteroatom interrupted alkylene; an arylene; a heteroarylene; or a combination thereof;

Y is an alkylene; a heteroatom interrupted alkylene; an arylene; a heteroarylene; or a combination thereof;

wherein the heteroatom interrupted alkylene and the heteroarylene have one or more heteroatoms selected from the group consisting of O, S, and N; and $R^1$ and $R^2$ are each independently H; substituted or unsubstituted linear, branched, or cyclic alkyl; one or more heteroatom interrupted substituted or unsubstituted linear branched or cyclic alkyl; unsubstituted or substituted aryl; unsubstituted or substituted heteroarylene; or a combination thereof; or $R^1$ and $R^2$ are combined as an alkylene or heteroatom interrupted alkylene, wherein $R^1NYNR^2$ comprises a heterocycle;

or a salt thereof.

2. The method according to claim 1, the bacterial infection being a mycobacterial infection.

3. The method according to claim 1, the bacterial infection being tuberculosis.

4. The method according to claim 1, the pharmaceutical composition further comprising an anti-tuberculosis drug.

5. The method according to claim 4, the anti-tuberculosis drug being selected from ciprofloxacin (CIP), clofazimine (CLZ), bedaquiline (BDQ), verapamil (VER), rifampin (RIF), ciprofloxacin (CIP), linezolid, isoniazid (INH), pyrazinamide (PZA), rifapentine (RPT), fluoroquinolones and ethambutol.

6. The method according to claim 1, the administration being oral, topical, subcutaneous, intraperitoneal, intravenous, intramuscular, or intradermal administration.

7. The method according to claim 1, wherein X is a combination of heteroatom interrupted alkylene and arylene.

8. The method according to claim 1, wherein Y is piperazine, oxyethylene, hexyl, oxydianiline, diiodo or phenylene.

9. The method according to claim 1, wherein n is 8; $R^1$ and $R^2$ are H; X is a combination of heteroatom interrupted alkylene and arylene; and Y is phenylene.

10. The method according to claim 1, wherein n is an integer from 3 to 20; X is a combination of heteroatom interrupted alkylene and arylene; Y is alkylene; heteroatom interrupted alkylene; arylene; or a combination thereof; and $R^1$ and $R^2$ are H.

11. The method according to claim 1, the OCG having a structure of

12. A method of inhibiting the growth of a *Mycobacterium*, the method comprising contacting the *Mycobacterium* with an OCG, the OCG comprising a general structure of:

wherein
n is an integer from 3 to 50;
X is an alkylene, a heteroatom interrupted alkylene; an arylene; a heteroarylene; or a combination thereof;
Y is an alkylene; a heteroatom interrupted alkylene; an arylene; a heteroarylene; or a combination thereof;
wherein the heteroatom interrupted alkylene and the heteroarylene have one or more heteroatoms selected from the group consisting of O, S, and N; and
$R^1$ and $R^2$ are each independently H; substituted or unsubstituted linear, branched, or cyclic alkyl;
one or more heteroatom interrupted substituted or unsubstituted linear branched or cyclic alkyl;
unsubstituted or substituted aryl; unsubstituted or substituted heteroarylene; or a combination thereof; or $R^1$ and $R^2$ are combined as an alkylene or heteroatom interrupted alkylene, wherein $R^1NYNR^2$ comprises a heterocycle;

or a salt thereof.

13. The method according to claim 12, the *Mycobacterium* being selected from *Mycobacterium tuberculosis, Mycobacterium smegmatis, Mycobacterium kansasii, Mycobacterium abscessus* (Mab), *Mycobacterium avium*, and *M. bovis*.

14. The method according to claim 12, wherein X is a combination of heteroatom interrupted alkylene and arylene; and/or wherein Y is piperazine, oxyethylene, hexyl, oxydianiline, diiodo or phenylene.

15. The method according to claim 12, wherein n is an integer from 3 to 20; X is a combination of heteroatom interrupted alkylene and arylene; Y is alkylene; heteroatom interrupted alkylene; arylene; or a combination thereof; and $R^1$ and $R^2$ are H; or $R^1$ and $R^2$ are combined as an alkylene or heteroatom interrupted alkylene, wherein $R^1NYNR^2$ comprises a heterocycle.

16. The method according to claim 12, the OCG having a structure of

17. A method of disrupting a mycobacterial membrane potential, the method comprising contacting a *Mycobacterium* with an OCG, the OCG comprising a general structure of:

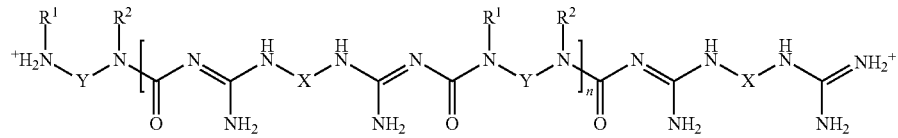

wherein
n is an integer ranging from 3 to 50;
X is an alkylene; a heteroatom interrupted alkylene; an arylene; a heteroarylene; or a combination thereof;
Y is an alkylene; a heteroatom interrupted alkylene; an arylene; a heteroarylene; or a combination thereof;
wherein the heteroatom interrupted alkylene and the heteroarylene have one or more heteroatoms selected from the group consisting of O, S, and N; and
$R^1$ and $R^2$ are each independently H; substituted or unsubstituted linear, branched, or cyclic alkyl; one or more heteroatom interrupted substituted or unsubstituted linear branched or cyclic alkyl; unsubstituted or substituted aryl; unsubstituted or substituted heteroarylene; or a combination thereof;
or a salt thereof.

18. The method according to claim 17, the *Mycobacterium* being selected from *Mycobacterium tuberculosis, Mycobacterium smegmatis, Mycobacterium kansasii, Mycobacterium abscessus* (Mab), *Mycobacterium avium*, and *M. bovis*.

19. The method according to claim 12, wherein X is a combination of heteroatom interrupted alkylene and arylene; and/or wherein Y is piperazine, oxyethylene, hexyl, oxydianiline, diiodo or phenylene.

20. The method according to claim 12, wherein n is an integer ranging from 3 to 20; X is a combination of heteroatom interrupted alkylene and arylene; Y is alkylene; heteroatom interrupted alkylene; arylene; or a combination thereof; and $R^1$ and $R^2$ are H.

* * * * *